(12) United States Patent
Chen et al.

(10) Patent No.: US 9,469,626 B2
(45) Date of Patent: Oct. 18, 2016

(54) BIOREFINING COMPOUNDS AND ORGANOCATALYTIC UPGRADING METHODS

(71) Applicant: Colorado State University Research Foundation, Fort Collins, CO (US)

(72) Inventors: Eugene Y. Chen, Fort Collins, CO (US); Dajiang Liu, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 285 days.

(21) Appl. No.: 13/934,074

(22) Filed: Jul. 2, 2013

(65) Prior Publication Data

US 2014/0007497 A1 Jan. 9, 2014

Related U.S. Application Data

(60) Provisional application No. 61/667,693, filed on Jul. 3, 2012, provisional application No. 61/698,171, filed on Sep. 7, 2012, provisional application No. 61/817,162, filed on Apr. 29, 2013.

(51) Int. Cl.
| | |
|---|---|
| C07D 307/00 | (2006.01) |
| C07D 407/06 | (2006.01) |
| C07D 307/12 | (2006.01) |
| C10L 1/02 | (2006.01) |
| C07D 307/46 | (2006.01) |

(52) U.S. Cl.
CPC ........... *C07D 407/06* (2013.01); *C07D 307/12* (2013.01); *C07D 307/46* (2013.01); *C10L 1/026* (2013.01); *Y02E 50/13* (2013.01); *Y02P 30/20* (2015.11)

(58) Field of Classification Search
CPC .................................................. C07D 407/06
USPC ....................................................... 549/429
See application file for complete search history.

(56) References Cited

U.S. PATENT DOCUMENTS

| 7,572,925 B2 | 8/2009 | Dumesic et al. | |
|---|---|---|---|
| 8,906,351 B2 * | 12/2014 | Scheurich ............... | A61Q 19/02 424/59 |
| 2009/0124839 A1 | 5/2009 | Dumesic et al. | |
| 2010/0279372 A1 | 11/2010 | Cho et al. | |

FOREIGN PATENT DOCUMENTS

| DE | 19704273 A1 | 9/1997 |
|---|---|---|
| WO | 2012/034629 A1 | 3/2012 |

OTHER PUBLICATIONS

Enders Chem. Rev. 2007, 107, 5606-5655.*
Zhao et al. Youji Huaxue (2010), 30(6), 912-917.*
Mohanazadeh et al. Phosphorus, Sulfur and Silicon and the Related Elements, 182(10), 2467-2475; 2007.*
Huang et al., "Production of high quality fuels from lignocellulose-derived chemicals: a convenient C-C bond formation of furfural, 5-methylfurfural and aromatic aldehyde," RSC Advances (Sep. 19, 2012) 2: 11211-11214.
Huber et al., "Production of Liquid Alkanes by Aqueous-Phase Processing of Biomass-Derived Carbohydrates," Science [www.sciencemag.org] (Jun. 3, 2005) 308: 1446-1450.
Liu et al., "Organocatalytic upgrading of the key biorefining building block by a catalytic ionic liquid and N-heterocyclic carbenes," Green Chem. (2012) 14: 2738-2746.
Liu et al., "Polymeric ionic liquid (PIL)-supported recyclable catalysts for biomass conversion into HMF," Biomass and Bioenergy (2013) 48: 181-190.
Sutton et al., "The Hydrodeoxygenation of bioderived furans into alkanes," Nature Chemistry (Apr. 7, 2013) 5: 428-432.
Zhang et al., "Ionic Liquid-Water Mixtures: Enhanced Kw for Efficient Cellulosic Biomass Conversion," Energy Fuels (Mar. 10, 2010) 24: 2410-2417.
International Search Report and Written Opinion for corresponding international application No. PCT/US2013/049147 mailed Oct. 31, 2013; 9 pages.
Huang, Yao-Bing et al., "Production of High Quality Fuels from Lignocellulose-Derived Chemicals: A Convenient C-C Bond Formation of Furfural, 5-Methylfurfural and Aromatic Aldehyde," RSC Advances, 2012, 2, 11211-11214.
Huber, George W. et al., "Production of Liquid Alkanes by Aqueous-Phase Processing of Biomass-Derived Carbohydrates," Science 308, 1446 (2005).
Liu, Dajiang et al., "Organocatalytic Upgrading of the Key Biorefining Building Block by a Catalytic Ionic Liquid and N-heterocyclic Carbenes," Journal (Online Computer File), 2012:1417271 (DN 157:638337); ISSN: 1463-9262, (pctus201349147 (CAPLUS)).
Liu, Dajiang et al., "Polymeric Ionic Liquid (PIL)-Supported Recyclable Catalysts for Biomass Conversion into HFM," Biomass and Bioenergy 48 (2013) 181-190.
Liu, Dajiang et al., "Organocatalytic Upgrading of the Key Biorefining Building Block by a Catalytic Ionic Liquid and N-heterocyclic Carbenes," Green Chemistry (2012), 14, pp. 2738-2746.
Sutton, Andrew D. et al., "The Hydrodeoxygenation of Bioderived Furans into Alkanes," Nature Chenmistry, vol. 5, May 2013.
Zhang, Yuetao et al., "Ionic Liquid—Water Mixtures: Enhanced Kw for Efficient Cellulosic Biomass Conversion," Energy Fuels 2010, 24, 2410-2417.

* cited by examiner

*Primary Examiner* — Nizal Chandrakumar
(74) *Attorney, Agent, or Firm* — Haukaas Fortius PLLC; Michael H. Haukaas

(57) ABSTRACT

The invention provides new methods for the direct umpolung self-condensation of 5-hydroxymethylfurfural (HMF) by organocatalysis, thereby upgrading the readily available substrate into 5,5'-di(hydroxymethyl)furoin (DHMF). While many efficient catalyst systems have been developed for conversion of plant biomass resources into HMF, the invention now provides methods to convert such nonfood biomass directly into DHMF by a simple process as described herein. The invention also provides highly effective new methods for upgrading other biomass furaldehydes and related compound to liquid fuels. The methods include the organocatalytic self-condensation (umpolung) of biomass furaldehydes into ($C_8$-$C_{12}$)furoin intermediates, followed by hydrogenation, etherification or esterification into oxygenated biodiesel, or hydrodeoxygenation by metal-acid tandem catalysis into premium hydrocarbon fuels.

5 Claims, 8 Drawing Sheets

BIOREFINING COMPOUNDS AND ORGANOCATALYTIC UPGRADING METHODS

RELATED APPLICATIONS

This application claims priority under 35 U.S.C. §119(e) to U.S. Provisional Patent Application Nos. 61/667,693 filed Jul. 3, 2012, 61/698,171 filed Sep. 7, 2012, and 61/817,162 filed Apr. 29, 2013, which applications are incorporated herein by reference.

GOVERNMENT SUPPORT

This invention was made with government support under Grant No. DE-FG02-10ER16193 awarded by the Department of Energy. The government has certain rights in the invention.

BACKGROUND OF THE INVENTION

Owing to their unique ability to dissolve lignocellulosic biomass and related carbohydrates under relatively mild conditions, plus several other concurrent advantages (e.g., as designable and recyclable solvents with low volatility and toxicity), ionic liquids (ILs) such as 1-alkyl(R)-3-methyl(M) imidazolium(IM) chloride salts, [RMIM]Cl, have attracted rapidly growing interest, particularly in the pursuit of renewable energy and sustainable chemicals from plant biomass. For instance, ILs have enabled homogenous hydrolysis of cellulose to sugars in high to quantitative conversion, in the presence or absence of catalyst, and catalyzed conversion of glucose or cellulose into the biomass platform chemical 5-hydroxymethylfurfural (HMF), a key and versatile biorefining intermediate for value-added chemicals and liquid fuels. Upgrading of HMF can be achieved by metal-catalyzed transformations such as hydrogenation/hydrogenolysis into 2,5-dimethylfuran, a liquid fuel with a 40% higher energy density than ethanol, and aldol condensation with organic compounds followed by dehydration/hydrogenation into $C_9$ to $C_{15}$ liquid alkanes (fuels), thus upgrading it into the kerosene/jet fuel range ($C_8$ to $C_{16}$). Direct coupling of two HMF molecules would make a $C_{12}$ biofuel intermediate, but HMF or furfural cannot undergo aldol self-condensation because they possess no α-H.

Accordingly, new methods are needed for upgrading HMF into useful intermediates and products. New methods for coupling HMF would provide such valuable intermediates for use as products such as chemicals for synthetic chemistry and liquids for jet or diesel fuels and the like.

SUMMARY

The invention also provides highly effective new methods for upgrading biomass furaldehydes and related compound to useful chemical intermediates and liquid fuels. The methods include the organocatalytic umpolung self-condensation of biomass furaldehydes into ($C_{10}$-$C_{12}$)furoin intermediates, followed by reactions such as hydrogenation, etherification or esterification, to provide oxygenated biodiesel, or hydrodeoxygenation by metal-acid tandem catalysis to provide premium hydrocarbon fuels.

For example, the invention also provides new methods for the direct umpolung self-condensation of 5-hydroxymethylfurfural (HMF) by organocatalysis, thereby upgrading the readily available substrate into 5,5'-di(hydroxymethyl)furoin (DHMF). While many efficient catalyst systems have been developed for conversion of plant biomass resources into HMF, the invention now provides methods to convert such nonfood biomass directly into DHMF and modified compounds thereof by simple processes as described herein.

Accordingly, the invention provides new compounds and methods as described below. In one embodiment, the invention provides a compound of Formula I:

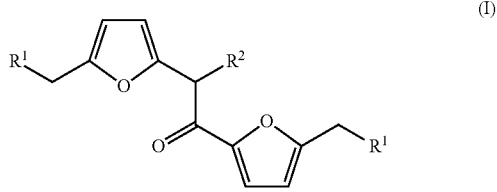

(I)

wherein each $R^1$ is independently H, OH, halo, amine, alkylamino, dialkylamino, alkoxy, or acyloxy; and $R^2$ is OH, halo, amine, alkylamino, dialkylamino, alkoxy, or acyloxy. In some embodiments, at least one $R^1$ is not H. In some embodiments, $R^2$ can be oxidized to provide a carbonyl, thereby providing the corresponding 1,2-diketone compound. In certain embodiments, the carbonyl of Formula (I) can be reduced to provide a hydroxyl, or a compound having an independently selected $R^2$ in place of the carbonyl oxygen.

In another embodiment, the invention provides a compound of Formula II:

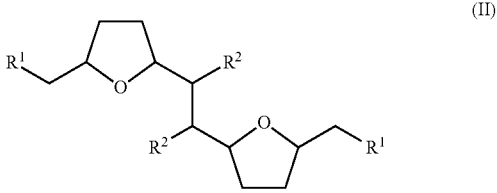

(II)

wherein $R^1$ is H, OH, halo, amine, alkylamino, dialkylamino, alkoxy, or acyloxy; and $R^2$ is H, OH, halo, amine, alkylamino, dialkylamino, alkoxy, or acyloxy. The invention also provides compositions that include one or more compounds of Formula (I) or (II) and one or more ($C_{10}$-$C_{22}$) alkanes.

The invention also provides an organocatalytic method to couple a furaldehyde compound, such as a compound of Formula (X), and a second furaldehyde compound. The method can include contacting a first furaldehyde compound and a second furaldehyde compound in the presence of an ionic liquid under conditions where the ionic liquid forms an N-heterocyclic carbene (NHC), or by contacting the furaldehydes in the presence of a discrete NHC, to provide a coupled product, such as a compound that includes a ($C_{10}$-$C_{12}$)furoin moiety. In some embodiments, the product will include a substituent at a furan 5-position, such as hydroxymethyl. In other embodiments, the product can include substituents at both the 5-position and the 5'-positions of the coupled furan products. The furans can be substituted on the furan ring at the 3, 4, 3', or 4' positions. The hydroxy group of a hydroxymethyl group at the 5-position and/or the 5'-position can further be modified, as described below.

In another embodiment, the invention provides an organocatalytic method to homocouple 5-hydroxymethylfurfural (HMF) comprising contacting HMF and an ionic liquid under conditions wherein the ionic liquid forms an N-heterocyclic carbene (NHC), or by contacting HMF and a discrete NHC, to provide 5,5'-di(hydroxymethyl)furoin (DHMF).

In yet another embodiment, the invention provides methods to prepare ($C_8$-$C_{22}$)alkanes. The methods can include contacting a compound of Formula I:

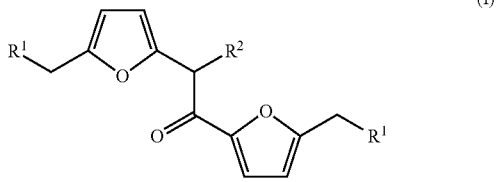

(I)

wherein $R^1$ and $R^2$ can be as described above for Formula (I); or contacting a compound of Formula II:

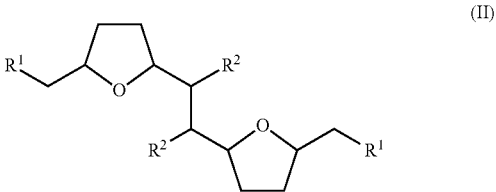

(II)

wherein $R^1$ and $R^2$ can be as described above for Formula (II); with a bifunctional catalyst systems that comprises a noble metal, such as palladium or platinum metal, and an acidic moiety under reaction conditions comprising heat and $H_2$ pressure in water; thereby reducing the compound of Formula (I) or (II) to provide one or more ($C_8$-$C_{22}$)alkanes. The acidic moiety can be, for example, a liquid or solid acid. In some embodiments, at least one $R^1$ of Formula (I) or Formula (II) is not H.

The invention thus provides novel compounds of the formulas described herein, intermediates for their synthesis, methods of preparing the compounds described herein, and useful downstream products of the compounds such as fuels and chemical intermediates.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
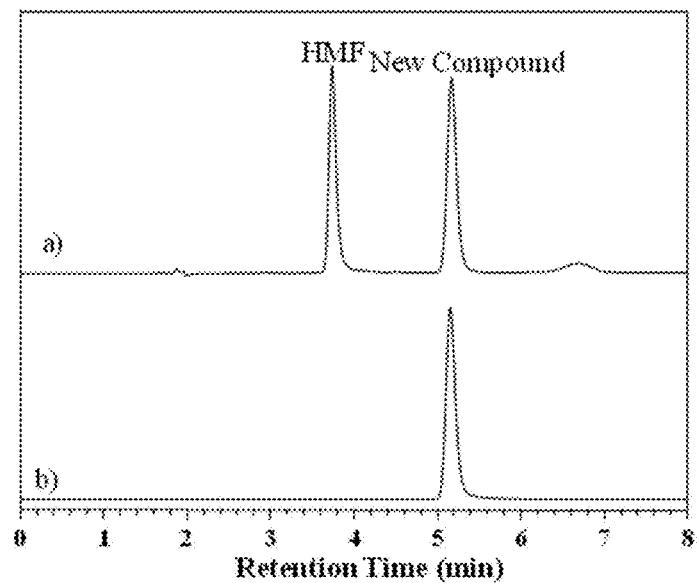
FIG. 1. Formation of a new compound (DHMF) as detected by HPLC from the HMF degradation reaction mixture in [EMIM]OAc at 80° C.: a) crude sample; b) after purification by silica gel column chromatography.

The invention provides new compounds and methods for preparing liquid alkanes and derivatives thereof in a targeted range from $C_{10}$ to about $C_{22}$. The compounds can be produced from biomass-derived carbohydrates such as 5-hydroxymethylfurfural (HMF), 5,5'-di(hydroxymethyl)furoin (DHMF), furoin, and similar furan compounds. The invention not only provides a route for using renewable biomass resources to diminish the reliance on petroleum-based liquid fuels, but it also provides a fuel with a specific range of carbon-atom chain lengths without the use of refining techniques. This latter feature makes the methods described herein especially attractive for producing alkane mixtures having defined characteristics, such as jet fuel, where specific physical properties are required (e.g., high energy density with narrow molecular weight distribution), that are unattainable with current biofuels. Thus, the invention provides catalytic processes for converting carbohydrates in general, and biomass-derived carbohydrates and byproducts in particular, to liquid, long-chain alkanes in the higher mass ranges (i.e., about $C_{10}$-$C_{22}$) that can be used, for example, as sulfur-free fuel components and as other valuable chemicals and intermediates.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage. For example, one or more substituents on a furan ring refers to one to four, one to three, or one to two, for example if the furan ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a chemical reaction or a physical change, e.g., in a solution or in a reaction mixture.

An "effective amount" refers to an amount effective to bring about a recited effect, such as an amount necessary to form products in a reaction mixture. Determination of a effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or substituted, for example, with a substituent described below. The alkyl can also be optionally partially or fully unsaturated. As such, the recitation of an alkyl group can include both alkenyl and alkynyl groups. The alkyl can be a monovalent hydrocarbon radical, as described and exemplified above, or it can be a divalent hydrocarbon radical (i.e., an alkylene).

The term "substituted" indicates that one or more hydrogen atoms on the group indicated in the expression using "substituted" or "optionally substituted" is replaced with a "substituent". The number referred to by 'one or more' can be apparent from the moiety on which the substituents reside. For example, one or more can refer to, e.g., 1, 2, 3, 4, 5, or 6; in some embodiments 1, 2, or 3; and in other embodiments 1 or 2, and if the substituent is an oxo group, two hydrogen atoms are replace by the presence of the substituent. The substituent can be one of a selection of indicated groups, or it can be a suitable group recited below or known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, (aryl)alkyl (e.g., benzyl or phenylethyl), heteroaryl, heterocycle, cycloalkyl, alkanoyl, alkoxycarbonyl, alkylcarbonyloxy, amino, alkylamino, dialkylamino, trifluoromethyl, trifluoromethoxy, trifluoromethylthio, difluoromethyl, acylamino, nitro, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano, as well as the moieties illustrated in the schemes and Figures of this disclosure, and combinations thereof. Additionally, suitable substituent groups can be, e.g., —X, —R, —O$^-$, —OR, —SR, —S$^-$, —NR$_2$, —NR$_3$, =NR, —CX$_3$, —CN, —OCN, —SCN, —N=C=O, —NCS, —NO, —NO$_2$, =N$_2$, —N$_3$, —NC(=O)R, —C(=O)R, —C(=O)NRR, —S(=O)$_2$O$^-$, —S(=O)$_2$OH, —S(=O)$_2$R, —OS(=O)$_2$OR, —S(=O)$_2$NR, —S(=O)R, —OP(=O)(OR)$_2$, —P(=O)(OR)$_2$, —OP(=O)(OH)(OR), —P(=O)(OH)(OR), —P(=O)(O$^-$)$_2$, —P(=O)(OH)$_2$, —C(=O)R, —C(=O)X, —C(S)R, —C(O)OR, —C(O)O$^-$, —C(S)OR, —C(O)SR, —C(S)SR, —C(O)NRR, —C(S)NRR, or —C(NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above can be excluded from the group of potential values for substituents on the substituted group. The various R groups in the schemes and figures of this disclosure can be one or more of the substituents recited above, thus the listing of certain variables for such R groups (including $R^1$, $R^2$, $R^3$, etc.) are representative and not exhaustive, and can be supplemented with one or more of the substituents above.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "acyloxy" refers to groups of the formula —O—C(=O)R, wherein R is an alkyl group as previously defined. Examples of acyloxy groups include acetoxy and propanoyloxy. The acyloxy can be unsubstituted or substituted. For example, the C1 (carbonyl) group of the acyloxy can be substituted with an aryl group, such as phenyl, to provide an aryl-substituted acyloxy, such as a benzoyl group.

The term "alcohol" refers to an at least mono-hydroxy-substituted alkane. A typical alcohol comprises a ($C_1$-$C_{12}$) alkyl moiety substituted at a hydrogen atom with one or more hydroxyl group. Alcohols include methanol, ethanol, n-propanol, i-propanol, n-butanol, i-butanol, s-butanol, t-butanol, n-pentanol, i-pentanol, hexanol, cyclohexanol, heptanol, octanol, nonanol, decanol, and the like. The carbon atom chain in alcohols can be straight, branched or cyclic. Alcohols can be mono-hydroxy, di-hydroxy, tri-hydroxy, and the like, as would be readily recognized by one of skill in the art.

A "monosaccharide" refers to any of the class of five-carbon or six-carbon sugars. Examples of monosaccharides include six-carbon polyols having the general chemical formula $C_{61}H_{12}O_6$. These compounds include aldohexoses which have an aldehyde functional group at position 1 or ketohexoses which have a ketone functional group at position 2. Example aldohexoses include allose, altrose, glucose, mannose, gulose, idose, galactose, and talose, in either D or L form.

Biorefining intermediates, such as reactants for an aldehyde coupling process, include 5-hydroxymethylfurfural (HMF) and related intermediates, such as furfural and other aldehyde (CHO)-containing organic compounds that can be derived from (bio)renewable resources such as cellulosic biomass.

Upgraded biofuel intermediates and liquid biofuels, such as products of the coupling reaction described herein, include compounds such as 5,5'-di(hydroxymethyl)furoin (DHMF, $C_{12}$), the product of upgrading HMF ($C_6$); DF (the coupling product of furfural); the coupling product of HMF and furfural; the coupling products of HMF with furaldehydes such as those of Formula X and other related furaldehydes; and furoins with different numbers of carbons and substitution patterns, depending on the starting material.

Products of the coupling reaction described herein, referred to as "coupling products" or "fuel intermediates" can be the furoin products resulting from the direct condensation (coupling) of two furaldehydes. The coupling can be made between the two same furaldehydes (homo-coupling) or two different furaldehydes (cross-coupling). The total number of carbons in the coupling products is the sum of the two furaldehydes employed, for example, homocoupling of the $C_6$ HMF forms $C_{12}$ 5,5'-di(hydroxymethyl)furoin (DHMF).

The term "furaldehydes" refers to biomass-derived furan aldehydes including, but not limited to, furfural ($C_5$), 5-methylfurfural ($C_6$), 5-hydroxymethylfurfural (HMF, $C_6$), and other aldehyde (CHO)-containing furans that can be derived from (bio)renewable resources such as cellulosic biomass. Furaldehydes and furaldehyde derivatives include compounds of Formula X:

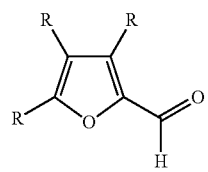

wherein each R is independently, for example, hydrogen, halo, hydroxy, nitro, amino, alkylamino, dialkylamino, ($C_1$-$C_{12}$)alkyl, hydroxy-($C_1$-$C_{12}$)alkyl, acyl-($C_1$-$C_{12}$)alkyl, ($C_1$-$C_{12}$)alkylcarbonyl-($C_1$-$C_{12}$)alkyl, and carboxy-($C_1$-$C_{12}$)alkyl, such as 5-hydroxymethylfurfural and furfural and substituted compounds thereof.

"Oxygenated diesel fuels" include polyols derived from hydrogenation of the coupling products. Examples include DHMF ethers derived from acid-catalyzed etherification of DHMF with ethanol and other alcohols, including mono-, di- and tri-ethers of DHMF and mixtures thereof; DHMF esters from esterification of DHMF with alkanoic acids or alkanoic anhydrides such as propionic anhydride, including mono-, di-, and tri-esters of DHMF and mixtures thereof.

A "high-quality hydrocarbon fuel" refers to a mixture of alkanes (linear, branched or cyclic) that can be used as a fuel source. Preferably, the alkanes are liquid and include about 10 to about 22 carbon atoms. The fuel can be derived from hydrodeoxygenation of the coupling products described herein. Preferably, the alkane mixture has a narrow alkane distribution and linear structure, and contains negligible or a minimum amount of oxygenated species. Narrow alkane distribution compounds can be prepared having precisely 8, 9, 10, 11, 12, 13, 14, 15, 16, 17, 18, 19, 20, 21, or 22 carbons, or ranges in between any two of the forgoing integers (e.g., 8-12, 10-16, 8-14, 12-20, 10-18, 16-22, etc.), especially 2-3 carbon ranges such as 10-12, 11-13, 12-14, 13-15, 14-16, and the like. In some embodiments, the fuel is absent of detectable amounts of sulfur.

An "ionic liquid" refers to a salt in the liquid state at ambient temperatures (for example, at least a liquid between 5° C. and 30° C., typically a liquid over a range of more than 100° C.), wherein the salt is composed of ions and/or short-lived ion pairs. Typically, an ionic liquid (IL) has a melting point below about 100° C. (212° F.). Useful cations of an ionic liquid that are useful in this invention are further described below. Useful anions for ionic liquids include acetate, halides including fluoride, chloride, bromide, and iodide, chlorate, nitrate, triflate, tosylate, tetrachloaluminate, tetrafluoroborate, hexafluorophosphate, anions such as [$^-$OH], [$^-$NTf$_2$], [$^-$N(CN)$_2$], [CH$_3$SO$_3^-$], [HCO$_2^-$], [$^-$C(=O)C(OH)Me], [HSO$_4^-$], [HCO$_3^-$], and the like.

A "noble metal" refers to a metal that is resistant to corrosion and oxidation in moist air, including copper, ruthenium, rhodium, palladium, silver, osmium, iridium, platinum, and gold. Noble metals can be used to aid reduction reactions, for example, in combination with an acid and a hydrogen gas atmosphere, and optionally with added heat.

Methods of the Invention

Biomass resources such as cellulose and glucose can be converted into HMF and other bio-refining intermediates by a variety of known techniques. See for example, the techniques described in Example 1 below, and U.S. Pat. No. 7,572,925 (Dumasic et al.). Bio-refining intermediates can be upgraded into biofuels and related intermediates by the organocatalytic methods described herein. One such method of the invention can be carried out by self-condensation (coupling) of HMF and/or other aldehyde-containing bio-refining intermediates, as well as cross-condensation (coupling) of two or more different intermediates, in the presence of a catalytic amount of a suitable and effective catalyst, at ambient temperature up to about 160° C., often at 60-80° C. Self-condensation of HMF cleanly provides 5,5'-di(hydroxymethyl)furoin (DHMF) in high yield. This product and others can be further efficiently converted into hydrocarbon fuels.

A variety of catalysts can be used to facilitate the coupling reactions as follows.

(a) Catalytic ionic liquids containing the acetate anion, such as 1-alkyl(R)-3-methyl(M)imidazolium(IM) acetate salts, [RMIM]OAc, which can self-release N-heterocyclic carbene (NHC) catalysts under the upgrading reaction conditions. A large number of different cations may be used. Typical nitrogen- or sulfur-based cations are acceptable, such as: 1-alkyl-3-methylimidazolium, 1-alkyl-3-alkylpyridinium (where the alkyl groups need not be the same), trialkylsulfonium, alkyl or aryl-substituted thiazolium salts, 1-alkyl-1-methylpyrrolidinium, 1,2-dialkylpyrazolium, dialkylmorpholinium, guanidinium, and 2-alkyl-isoquinolinium.

(b) Discrete NHCs such as 1,3,4-triphenyl-4,5-dihydro-1H-1,2,4-triazol-5-ylidene (TPT), 1,3-di-mesityl-butyl-imidazolin-2-ylidene (IMes), 1,3-dialkylimidazolin-2-ylidene, and other related NHC and carbene species. Other discrete NHCs derived from salts of dialkyl or diaryl imidazolium, aryl substituted triazolium, and alkyl or aryl substituted thiazolium, can also be used for the coupling reaction.

(c) 1-Alkyl(R)-3-methyl(M)imidazolium(IM) chloride salts, [RMIM]Cl, in the presence of an organic or inorganic base such as DBU (1,8-diazabicyclo[5.4.0]undec-7-ene) or an alkali metal alkoxide such as KOtBu, which can deprotonate C2-H protons under the reaction conditions to generate the carbene catalyst in situ. Other suitable bases include alkali metal hydrides such as NaH or KH, or an alkali metal hexamethyldisilazane such as potassium hexamethyldisilazane (KHMDS).

Conversion of the condensation (coupling) products into liquid jet fuel, various different grades of biofuels, polyols, or oxygenated diesel fuels, can be carried out by chemical transformations such as hydrogenation, dehydration, etherification, esterification, and various combinations thereof. Examples of these transformations include: (a) hydrogenation of DHMF into DHM-THF-EG; (b) etherification of DHMF into ethers of DHMF including, for example, mono-, di- and tri-ethers of DHMF; and (c) esterification of DHMF to esters of DHMF including, for example, mono-, di-, and tri-esters of DHMF. Common hydrogenation catalysts such as Pd/C can be employed for hydrogenation, and common acids, including solid acids, can be used for etherification. In one embodiment, the condensation (coupling) product DHMF can be converted into premium alkane fuels by hydrodeoxygenation in the presence of a bifunctional metal-acid catalyst. Bifunctional catalysts are those with both metal and acid sites (e.g., noble metal on acidic support).

Specific examples of bifunctional catalysts include Pt/CsH$_2$PW$_{12}$O$_{40}$, and Pt/C with TaOPO$_4$.

Accordingly, in one embodiment, the invention provides a compound of Formula I:

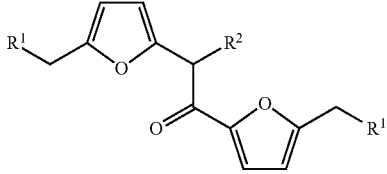

(I)

wherein each R$^1$ is independently H, OH, halo, nitro, amine, alkylamino, dialkylamino, alkoxy, or acyloxy; and R$^2$ is OH, halo, nitro, amine, alkylamino, dialkylamino, alkoxy, or acyloxy; provided that at least one R$^1$ is not H. In another embodiment, the 3- or 4-position of a furan ring of Formula (I) can be substituted as described for Formula (X). The compound can be a mono-, di-, or tri-ether, or a mono-, di-, or tri-ester. Thus, compounds of Formula (I) can be, for example, compounds of Formula (IA), (IB), or (IC):

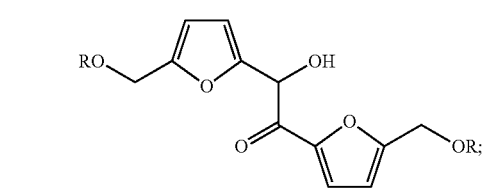

(IA)

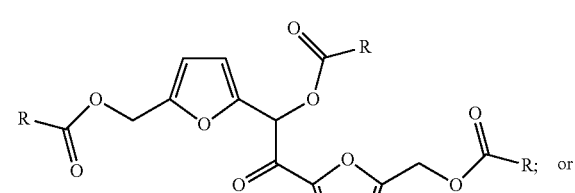

(IB)

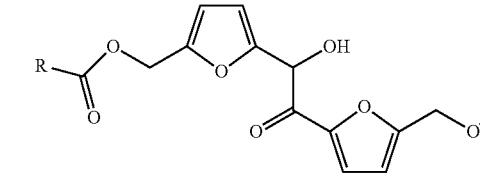

(IC)

wherein each R is independently aryl or (C$_1$-C$_{12}$)alkyl, where the alkyl can be straight, branched, or cyclic, and the alkyl and/or aryl can be optionally substituted as described above for the definition of substituted, or an R$^1$ as defined for Formula (I). Specific examples of compounds of Formulas (I), (IA), and (IB) include:

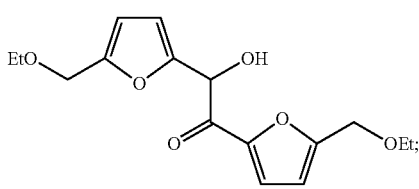

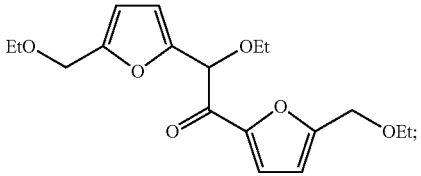

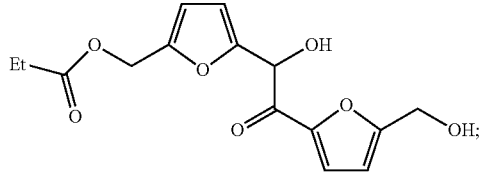

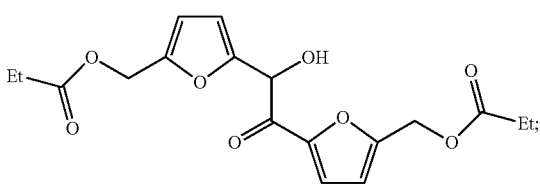

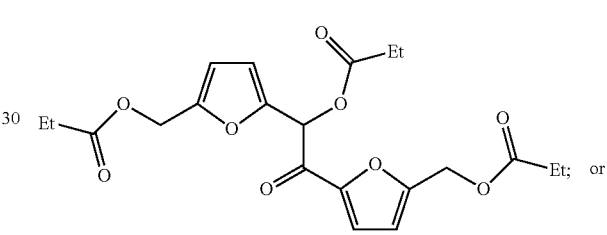

or

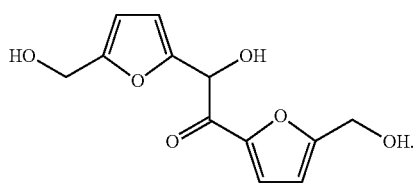

In another embodiment, the invention provides compounds of Formula II:

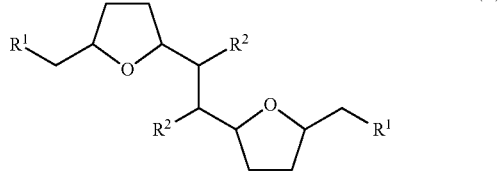

(II)

wherein R$^1$ is H, OH, halo, amine, alkylamino, dialkylamino, alkoxy, or acyloxy; and R$^2$ is H, OH, halo, amine, alkylamino, dialkylamino, alkoxy, or acyloxy. In some embodiments, at least one R$^1$ is not H. In various embodiments, at least one R$^2$ is not H. In certain embodiments, at least one R$^2$ is not OH.

Compounds of Formula (II) can be, for example, compounds of Formulas (IIA), (IIB), or (IIC):

(IIA)

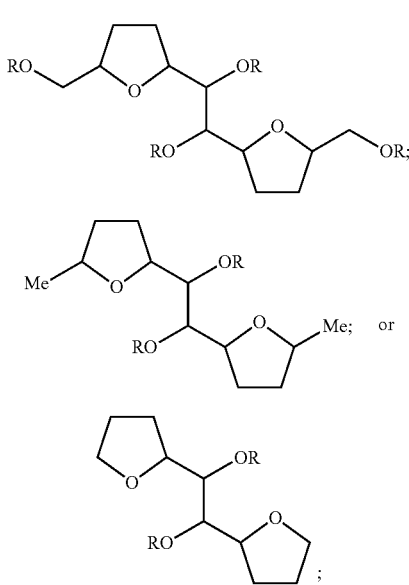

(IIB)

(IIC)

wherein each R is independently H, alkyl, or acyl, or $R^1$ as defined for Formula (II) above. Thus, the compound can be a mono-, di-, tri-, or tetra-ether (e.g., Formula IIA), or a mono- or di-ether (e.g., Formula IIB or IIC). The compounds can also be mono-, di-, tri-, or tetra-esters (e.g., Formula IIA), or mono- or di-esters (e.g., Formula IIB or IIC). Specific examples of Formulas (II), (IIA), (IIB), or (IIC) include:

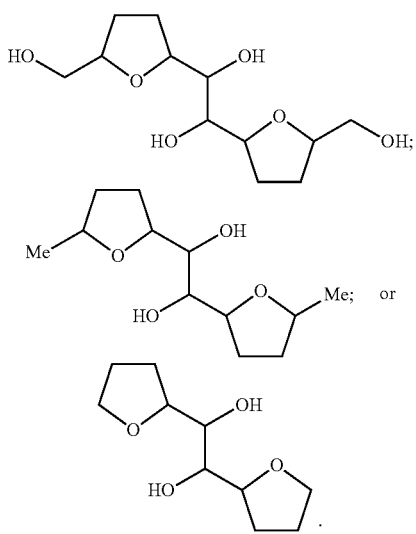

As to any of the formula and structures above, any available hydroxy group, R, $R^1$, or $R^2$ can be, or can be converted to, an ether or an ester moiety. Accordingly, a variety of monoethers, diethers, triethers, tetraethers, monoesters, diesters, triesters, and tetraesters can be provided. Additionally, compounds that include both ether and ester moieties can be prepared, by controlling the order and stoichiometry of reaction conditions, as can be determined by one of skill in the art.

Under oxidative work-up conditions, for example, with air-oxidation, added oxidants, or the like, compounds of Formula (III) and (IV) can also be prepared:

(III)

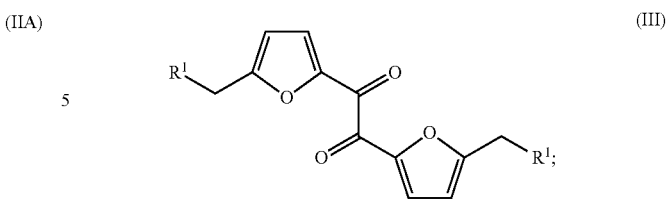

wherein each $R^1$ is independently H, OH, halo, nitro, amine, alkylamino, dialkylamino, alkoxy, or acyloxy. In some embodiments, at least one $R^1$ is not H, and/or at least one $R^1$ is not OH. In various embodiments, the 3- or 4-position of a furan ring of Formula (I) can be substituted as described for Formula (X).

By carrying out a selective hydrogenation reaction on Formula (I) or (II), for example, with additional heat or under longer reaction times for the preparation of Formula (II), a compound of Formula (IV) can be prepared, where one $R^2$ is at least initially OH:

(IV)

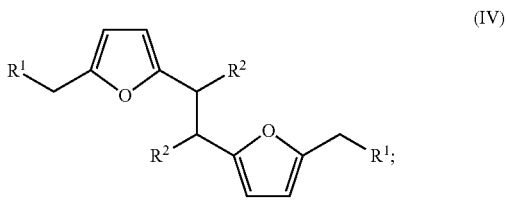

wherein each $R^1$ is independently H, OH, halo, nitro, amine, alkylamino, dialkylamino, alkoxy, or acyloxy; and each $R^2$ is independently OH, halo, nitro, amine, alkylamino, dialkylamino, alkoxy, or acyloxy. In some embodiments, at least one $R^1$ is not H, and/or at least one $R^1$ is not OH. In another embodiment, the 3- or 4-position of a furan ring of Formula (I) can be substituted as described for Formula (X).

Compounds and formulas above that include a hydroxymethyl group at a furan or tetrahydrofuran 5- or 5'-position can be modified to oxidize the hydroxymethyl group to a carbonyl moiety, substituted by a hydroxyl, alkoxy, or amino group using known oxidative transformations. As would be recognized by one of skill in the art, amino groups can be optionally protected, for example, with a nitrogen protecting group such as acetate, benzyl, benzyloxy, and the like.

The invention further provides a composition comprising one or more compounds or compounds of a formula described above, in combination with one or more ($C_8$-$C_{22}$) alkanes, or ($C_{10}$-$C_{22}$)alkanes.

The invention also provides an organocatalytic method to couple a first furaldehyde compound, such as a compound of Formula (X), and a second furaldehyde compound, such as a second compound of Formula (X). The compounds can be the same or different. The method can include contacting a first furaldehyde compound and a second furaldehyde compound in the presence of an ionic liquid under conditions where the ionic liquid forms an N-heterocyclic carbene (NHC), or by contacting the furaldehydes in the presence of a discrete NHC, to provide a coupled product, such as a compound that includes a ($C_{10}$-$C_{12}$)furoin moiety. In some embodiments, the product will include a substituent at a furan 5-position, such as hydroxymethyl. In other embodiments, the product can include substituents at both the 5-position and the 5'-positions of the coupled furan products. The furans can be substituted on the furan ring at the 3, 4, 3', or 4' positions. The hydroxy group of a hydroxymethyl group at the 5-position and/or the 5'-position can further be modified, as described herein, such as by oxidation, conjugation, or reduction.

In another embodiment, the invention provides an organocatalytic method to homocouple 5-hydroxymethylfurfural (HMF) comprising contacting HMF and an ionic liquid under conditions wherein the ionic liquid forms an N-heterocyclic carbene (NHC), or by contacting HMF and a discrete NHC, to provide 5,5'-di(hydroxymethyl)furoin (DHMF).

The ionic liquid cation can be a 1-alkyl-3-methylimidazolium, 1-alkyl-3-alkylpyridinium, trialkylsulfonium, alkyl-substituted thiazolium, aryl-substituted thiazolium, 1-alkyl-1-methylpyrrolidinium, 1,2-dialkylpyrazolium, dialkylmorpholinium, guanidinium, or 2-alkyl-isoquinolinium. For ionic liquid cations, each alkyl can be independently ($C_1$-$C_{12}$)alkyl, for example, methyl, ethyl, propyl, or butyl. Aryl can be as defined for aryl above, for example, phenyl. Anions of the ionic liquid can be acetate, halide, or an anion as described above in the definition of ionic liquids. Any suitable and effective combination of cation and anion that facilitates the umpolung coupling of furaldehydes can be employed.

In one embodiment, the ionic liquid can be a 1-alkyl-3-methyl-imidazolium halide salt in the presence of an organic or inorganic base, wherein the base is capable of deprotonating a C2-H proton of the ionic liquid under the reaction conditions to generate a carbene catalyst in situ. For example, the ionic liquid can be a 1-alkyl-3-methyl-imidazolium acetate salt. In certain specific embodiments, the ionic liquid is [EMIM]OAc, or [EMIM]Cl in the presence of a base. The base can be, for example, DBU, an alkali metal alkoxide, an alkali metal hydride, or an alkali metal hexamethyldisilazane. Specific examples include NaOMe, KOMe, NaOtBu, KOtBu, LiH, NaH, KH, NaHMDS, or KHMDS.

A variety of different discrete NHCs can be employed in the methods described herein. Examples of such discrete NHCs include salts of dialkyl or diaryl imidazolium, aryl substituted triazolium, and alkyl or aryl substituted thiazolium. In one embodiment, the discrete NHC is 1,3,4-triphenyl-4,5-dihydro-1H-1,2,4-triazol-5-ylidene (TPT). In another embodiment, the discrete NHC is 1,3-di-mesityl-butyl-imidazolin-2-ylidene (IMes). In another embodiment, the discrete NHC is a 1,3-dialkylimidazolin-2-ylidene.

After the coupling product has formed, the product can be further modified by hydrogenation, hydrogenolysis, hydrodeoxygenation, etherification, esterification, or combinations thereof. The products can be used as liquid fuels.

For example, the invention provides for hydrogenating DHMF to provide a liquid comprising 1,2-di(5-hydromethyltetrahydrofuran-2-yl)ethylene glycol. The product can be conjugated to provide mono-, di-, or tri-ethers, mono-, di-, or tri-esters, or combinations of such moieties on the product of the reaction.

An organic solvent can be used in the coupling reaction. However, the ionic liquid can also act as a solvent for the reaction system. Thus, the method can be carried out under otherwise solvent-free conditions, or in the absence of an organic solvent.

The invention further provides a method to prepare a ($C_8$-$C_{22}$)alkane, or a ($C_{10}$-$C_{22}$)alkane, comprising contacting a compound of Formula I:

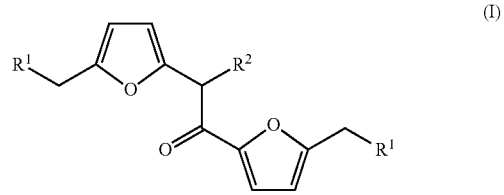

wherein each $R^1$ and $R^2$ is as defined for Formula (I) above; or contacting a compound of Formula II

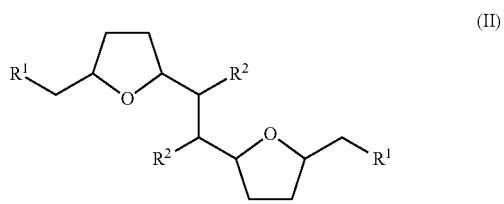

wherein $R^1$ and $R^2$ can be as described above for Formula (II); with a bifunctional catalyst systems that comprises a noble metal, such as palladium or platinum metal, and an acidic moiety under reaction conditions comprising heat and $H_2$ pressure in water; thereby reducing the compound of Formula (I) or (II) to provide one or more ($C_8$-$C_{22}$)alkanes or one or more ($C_{10}$-$C_{22}$)alkanes. The acidic moiety can be, for example, a liquid or solid acid. In some embodiments, at least one $R^1$ of Formula (I) or Formula (II) is not H. In some embodiments, the product is exclusively a hydrocarbon.

The method above can also be used to prepare compounds of Formula (IV), where the carbonyl of the intermediate is selectively reduced over the aromatic furan rings. Thus, in some embodiments, the product can include no more than 1, 2, 3, 4, 5, 6, 7, or 8 oxygen atoms per product molecule, depending on the reaction conditions employed and the desired products of the reaction.

In one specific embodiment, the compound of Formula (I) is 5,5'-di(hydroxymethyl)furoin (DHMF). In some embodiments, the bifunctional catalyst system is an acidic aqueous solution of an inorganic acid and a noble metal. The noble metal can provide support for the acid, or the noble metal can be adsorbed onto carbon black (e.g., metal/C). In some embodiments, the bifunctional catalyst system is an acidic solution of aqueous $H_3PO_4$ and Pd/C; a heteropoly acid of the formula $CsH_2PW_{12}O_{40}$ supported Pt; or an acidic solid catalyst of the formula $TaOPO_4$ in combination with Pt/C.

In one specific embodiment, the compound of Formula (I) is 5,5'-di(hydroxymethyl)furoin (DHMF), the bifunctional catalyst system is an acidic solid catalyst of the formula $TaOPO_4$ in combination with Pt/C, wherein ($C_{10}$-$C_{22}$)alkanes are produced with at least 90% selectivity.

Suitable temperatures for use with the bifunctional catalyst include at least about 150° C., at least about 175° C., at least about 200° C., at least about 250° C., or at least about 275° C. For example, suitable temperature ranges include about 150° C. to about 350° C., about 200° C. to about 325° C., about 250° C. to about 325° C., or about 300° C. Lower temperatures typically merely require longer reaction times. The reaction with the bifunctional catalyst can be carried out under any suitable and effective pressure of hydrogen gas, such as at least about 1.5 MPa, as at least about 1.7 MPa, as at least about 2 MPa, as at least about 2.5 MPa, or at about 3 MPa. Greater pressures of hydrogen gas can be employed to further shorten reaction time. Lesser pressures of hydrogen gas can be employed but typically require longer reaction times.

General Synthetic Methods

The invention provides methods of making the compounds and compositions of the invention. The compounds and compositions can be prepared by any of the applicable techniques described herein, optionally in combination with standard techniques of organic synthesis. Many techniques such as etherification and esterification are well known in the art. However, many of these techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6; as well as standard organic reference texts such as *March's Advanced Organic Chemistry: Reactions, Mechanisms, and Structure*, 5$^{th}$ Ed., by M. B. Smith and J. March (John Wiley & Sons, New York, 2001); *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing); *Advanced Organic Chemistry, Part B: Reactions and Synthesis, Second Edition*, Cary and Sundberg (1983); *Protecting Groups in Organic Synthesis, Second Edition*, Greene, T. W., and Wutz, P. G. M., John Wiley & Sons, New York; and *Comprehensive Organic Transformations*, Larock, R. C., Second Edition, John Wiley & Sons, New York (1999).

A number of exemplary methods for preparation of compounds and compositions of the invention are provided below. These methods are intended to illustrate the nature of such preparations are not intended to limit the scope of applicable methods.

Generally, the reaction conditions such as temperature, reaction time, solvents, work-up procedures, and the like, will be those common in the art for the particular reaction to be performed. The cited reference material, together with material cited therein, contains detailed descriptions of such conditions. Typically the temperatures will be −100° C. to 400° C., as necessary for the reaction of interest, solvents if required will be aprotic or protic depending on the conditions required, and reaction times can be about 1 minute to about 10 days. Work-up typically consists of quenching any unreacted reagents followed by partition between a water/organic layer system (extraction) and separation of the layer containing the product of interest.

Oxidation and reduction reactions are typically carried out at temperatures near room temperature (about 23° C.), although for metal hydride reductions frequently the temperature is reduced to 0° C. to −100° C. Heating can also be used when appropriate to facilitate completion of the reaction or to increase conversion of substrates. Solvents are typically aprotic for reductions and may be either protic or aprotic for oxidations. Reaction times are adjusted to achieve desired conversions.

The formulas and compounds described herein can be modified using protecting groups. Suitable amino and carboxy protecting groups are known to those skilled in the art (see for example, T. W. Greene, *Protecting Groups In Organic Synthesis*; Wiley: New York, Third Edition, 1999, and references cited therein; Philip J. Kocienski; *Protecting Groups* (Georg Thieme Verlag Stuttgart, New York, 1994); and references cited therein).

Ionic liquids and their reactions are further described in the reference literature. These known techniques and conditions can be used to carry out and modify reactions and compounds described herein. Useful information has been described by, for example, Wasserscheid and Keim, *Angew. Chem. Int. Ed.* 2000, 39, 3772; Welton, *Chem. Rev.* 1999, 99, 2071, *Ionic Liquids in Synthesis*, Wasserscheid and Welton, Eds., Wiley-VCH (2002); and *Molten Salt Chemistry*, Mamantov and Marassi, Eds., NATO ASI Series C, Mathematical and Physical Sciences Vol. 202, D. Reidel Publishing Co. (1986); and references cited therein.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Materials, Reagents, and Methods

Syntheses and manipulations of air- and moisture-sensitive materials were carried out in flamed Schlenk-type glassware on a dual-manifold Schlenk line, on a high-vacuum line, or in an inert gas (Ar or $N_2$)-filled glovebox. HPLC-grade organic solvents were first sparged extensively with nitrogen during filling 20 L solvent reservoirs and then dried by passage through activated alumina (for $Et_2O$, THF, and $CH_2Cl_2$) followed by passage through Q-5 supported copper catalyst (for toluene and hexanes) stainless steel columns HPLC-grade DMF was degassed and dried over $CaH_2$ overnight, followed by vacuum distillation ($CaH_2$ was removed before distillation). DMSO-$d_6$ was first degassed and dried over $CaH_2$, followed by vacuum distillation. NMR-scale reactions were conducted in Teflon-valve-sealed J. Young-type NMR tubes with hexamethylbenzene as the internal standard. NMR spectra were recorded on a Varian Inova 300 (FT 300 MHz, $^1H$; 75 MHz, $^{13}C$) or a Varian Inova 400 MHz spectrometer. Chemical shifts for $^1H$ and $^{13}C$ spectra were referenced to internal NMR solvent residual resonances and are reported as parts per million relative to $SiMe_4$.

High-resolution mass spectrometry (HRMS) data were collected on an Agilent 6220 Accurate time-of-flight LC/MS spectrometer. Elemental analyses were carried out by Robertson Microlit Laboratories, Madison, N.J.

The water-soluble products were analyzed by Agilent 1260 Infinity HPLC system equipped with either an Agilent Eclipse Plus C18 Column (100×4 6 mm; 80/20 water/methanol, 0.6 ml/min, 30° C.) with a UV detector (284 nm) for 5-hydroxymethylfurfural (HMF) and 5,5'-di(hydroxymethyl)furoin (DHMF) detection and quantification, or a Biorad Aminex HPX-87H Column (300×7.8 mm; water, 0.6 ml/min, 45° C.) with an Agilent 1260 Infinity ELSD detector (65° C., 3.5 bar, gain 6) for glucose and other sugars detection.

Hydrogenation and HDO reactions were carried out in a Parr 4842 pressure reactor (Parr Instrument Co.). The organic products extracted by dichloromethane (DCM) were analyzed either by an Agilent 6890N GC-FID system with a Durabond DB-5 ms column (30 m, 0.25 mm I.D., 0.25 μm film) or by an Agilent 6890 GC-MS system equipped with a Phenomenex Zebron ZB-5 ms column (30 m, 0.25 mm I.D., 0.25 μm film). Heating values were measured by a Petrolab C2000 calorimeter. Any DHMF remained in the water phase after HDO was analyzed with an Agilent Eclipse Plus C18 Column (100×4 6 mm; 80/20 water/methanol, 0.6 mL/min, 30° C.) and a UV detector (284 nm).

D-Glucose (Granular powder, Fisher Chemical), $CrCl_2$ (Alfa Aesar), HMF (Acros Organics), hexamethylbenzene (Alfa Aesar), 1,8-diazabicyclo [5.4.0]undec-7-ene (DBU, Acros Organics), acetic acid (Mallinckrodt Chemicals, ACS grade), silver acetate (Strem Chemical) were used as received. N-Heterocyclic carbenes (NHCs), 1,3-bis(2,4,6-trimethyl-phenyl)imidazol-2-ylidene (IMes) and 1,3-di-tert-butylimidazol-2-ylidene (I$^t$Bu), were purchased from Strem Chemical Co. Literature procedures were used to prepare 1,3,4-triphenyl-4,5-dihydro-1H-1,2,4-triazol-5-ylidene (TPT) (Enders et al., *Angew. Chem., Int. Ed. Engl.* 1995, 34, 1021; Enders et al., *Synthesis* 2003, 1292-1295), while 1-ethyl-2,3-dimethylimidazolium acetate ([EDMIM]OAc) (Brandt et al., *Green Chem.* 2010, 12, 672-679) was prepared using an anion exchange route (vide infra). 1-Ethyl-3-methylimidazolium acetate ([EMIM]OAc, Aldrich) and 1-ethyl-2,3-dimethylimidazolium chloride ([EDMIM]Cl, Aldrich) were dried under vacuum at 100° C. for 24 hours. 1-Ethyl-3-methylimidazolium chloride ([EMIM]Cl, Fluka) was dried under vacuum at 100° C. for 24 hours, followed by repeated recrystallization from $CH_2Cl_2$ and hexanes at room temperature. The purified ionic liquids were stored in an argon-filled glovebox.

Additionally, furfural (Alfa Aesar), 5-methylfurfural (MF, Alfa Aesar), 5-hydroxymethylfurfural (HMF, Acros Organics), $H_3PO_4$ (85 wt % aqueous solution, Sigma Aldrich), $Ta_2O_5$ (Alfa Aesar), $Cs_2CO_3$ (Alfa Aesar), $H_3PW_{12}O_{40} \cdot xH_2O$ (Alfa Aesar), $PtCl_4$ (Acros Organics), Pd/C and Pt/C (5 wt %, Alfa Aesar), and 1,3-bis(2,4,6-trimethylphenyl)-1,3-dihydro-2H-imidazol-2-ylidene (IMes) (Sigma Aldrich) were purchased and used as received. $TaOPO_4$ and $Cs_xH_{3-x}PW_{12}O_{40}$ (x=1 and 2.5) were prepared according to literature procedures (Huang et al., *RSC Advances*, 2012, 2, 11211; Tian et al., *Chem. Eng. Technol.* 2011, 34, 482). The supported 4 wt % $Pt/Cs_xH_{3-x}PW_{12}O_{40}$ catalyst was prepared by incipient wetness impregnation, which was dried in an oven at 120° C. overnight and reduced under flowing $H_2$ (100 mL/min) at 250° C. for 3 hours before use.

Example 1

Conversion of Biorefining Intermediates to Value-Added Chemicals

The acetate-based room-temperature (RT) IL, [EMIM]OAc, has been identified as a better solvent than chloride-based ILs for biomass solution processing (i.e., dissolution, fractionation, and re-precipitation), due to its lower melting point, viscosity and corrosive character as well as higher loading and non-toxicity. However, for biomass conversion into sugars and HMF, the chloride-based ILs such as [RMIM]Cl (R=Et, $^n$Bu) are preferred solvents, and we have found [EMIM]OAc is completely ineffective for the glucose (or cellulose)-to-HMF conversion (Liu and Chen, *Appl. Catal. A: Gen.* 2012, 435/436, 78). A recent report disclosed that [EMIM]OAc rapidly degrades HMF (>99% degradation at 100° C. after 8 h), but the degradation mechanism was not proposed and the degradation product was not identified (Stahlberg et al., *Green Chem.* 2010, 12, 321).

We found that [EMIM]OAc also rapidly degrades glucose (70% degradation at 100° C. after 1 hour), as described below. We therefore hypothesized that the observed rapid HMF degradation in [EMIM]OAc may be rendered by N-heterocyclic carbene (NHC) catalysis, because it is known that a small concentration of carbene exists in this IL with the basic acetate anion, as demonstrated experimentally by its carbene-type reaction with elemental sulfur or selenium and as catalyst for benzoin condensation of benzaldehyde. While addressing the mechanism of HMF degradation in [EMIM]OAc, we discovered that this "harmful" degradation process can be utilized for highly efficient upgrading of HMF into a high-value biorefinery product, 5,5'-di(hydroxymethyl)furoin (DHMF)—a kerosene/jet fuel intermediate, through NHC-catalyzed self-condensation enabled by this organocatalytic IL. Subsequent use of a discrete NHC (1-5 mol %), the Enders triazolylidene carbene TPT (1,3,4-triphenyl-4,5-dihydro-1H-1,2,4-triazol-5-ylidene) (Enders et al., *Synthesis* 2003, 1292-1295), leads to rapid (1 h), highly selective and high-yield synthesis of DHMF from HMF. The in situ generated NHC by treating the chloride-based IL [EMIM]Cl with an organic base also rapidly upgrades HMF into DHMF in high yield (96%).

HPLC monitoring of the HMF degradation in [EMIM]OAc (1:1 molar ratio) in a shaker revealed rapid degradation of HMF even at temperatures far below 120° C., a typical temperature employed for biomass conversion. For example, 70% and 94% of HMF has been degraded after 1 h at 50° C. and 80° C., respectively. The degradation kinetics at 80° C. was examined with NMR by performing the degradation in DMSO-$d_6$ in a J. Young-type NMR tube with a 1/1 HMF/[EMIM]OAc molar ratio and using hexamethylbenzene as the internal standard. A first-order kinetic plot of the initial degradation process (2-15 minutes) yielded a rate constant of k=0.085 min$^{-1}$ at 80° C., corresponding to a degradation half-life of 8.2 minutes at this temperature.

Figure 2:
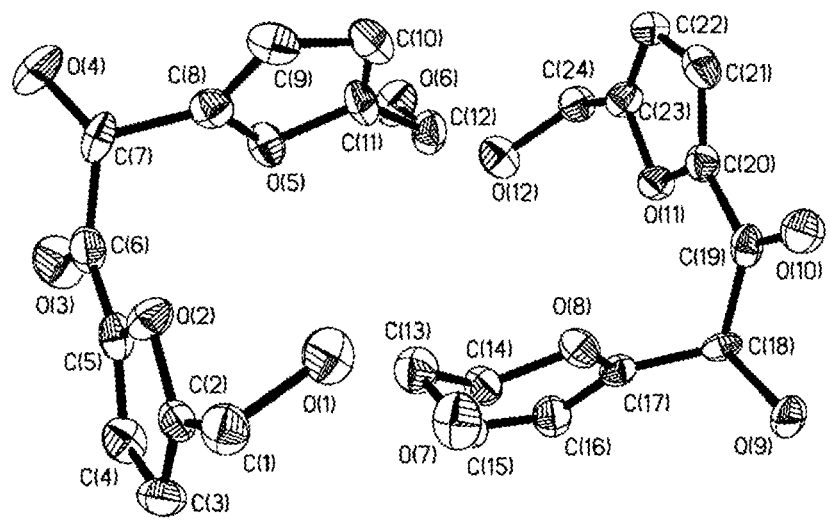
FIG. 2. X-ray crystal structure of 5,5'-di(hydroxymethyl) furoin (DHMF) showing two independent molecules associated with each by moderate hydrogen bonds with minor structural differences in the unit cell. Hydrogen atoms have been omitted for clarity and ellipsoids drawn at 50% probability.

Parallel scale-up runs clearly showed formation of a new compound as the predominant product (by HPLC, FIG. 1), with a yield of 72% at HMF conversion of 86% at 80° C. Subsequent separation and purification afforded the pure compound (FIG. 1) in 50% isolated yield. This compound is stable in water and air, as it was isolated from the aqueous medium and no decomposition or oxidation was observed after exposing the solid sample to air for a week. NMR and MS data, detailed below, clearly indicate it is a $C_{12}$ furoin, DHMF, the molecular structure of which has been confirmed by X-ray diffraction analysis (FIG. 2).

Structural data clearly show a C=O double bond for C(6) with a bond length of 1.224(7)Å and a CH—OH single bond for C(7) with a bond length of 1.420(10)Å, the latter of which is identical to the terminal $CH_2$—OH bond distance [e.g., C(12)-O(6)H=1.420(6)Å]. This assignment is further confirmed by the sum of the angles around C(6) (carbonyl) and C(7) (hydroxyl) carbons of 360.1° and 332.3°, for sp$^2$-hybridized trigonal-planar and sp$^3$-hybridized tetrahedral carbon centers, respectively. CCDC-887451 contains the supplementary crystallographic data for DHMF. These data can be obtained free of charge from The Cambridge Crystallographic Data Centre via www.ccdc.cam.ac.uk/data_request/cif.

The identification and characterization of the structure of the main product formed from the HMF degradation in [EMIM]OAc prompted us to realize that DHMF is the umpolung condensation product of HMF catalyzed by [EMIM]OAc. The catalytic cycle for this unique process enabled by the organocatalytic [EMIM]OAc is proposed in FIG. 3 and the general reaction is shown below in Scheme 1.

Scheme 1. Coupling Reaction for Preparation of DHMF.

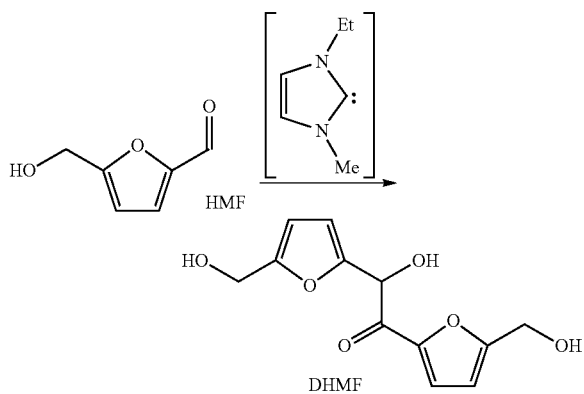

The catalyst in this carbene catalysis is 1-ethyl-3-methylimidazolin-2-ylidene carbene I (FIG. 3), present in the [EMIM]OAc equilibrium that favors the ion pair form. The early steps of the proposed elementary reactions involved in the catalysis deviate somewhat from those put forth for the NHC-catalyzed umpolung of aldehydes and α,β-unsaturated esters, due to the important role of HOAc, which co-exists with carbene I in the [EMIM]OAc equilibrium. Specifically, nucleophilic addition of the carbene I to the carbonyl group of HMF generates a zwitterionic tetrahedral intermediate, which is protonated by HOAc to afford a 2-(5-hydroxymethyl-2-α-hydroxyfuranyl)imidazolium acetate salt, the resting intermediate II.

Figure 3A:
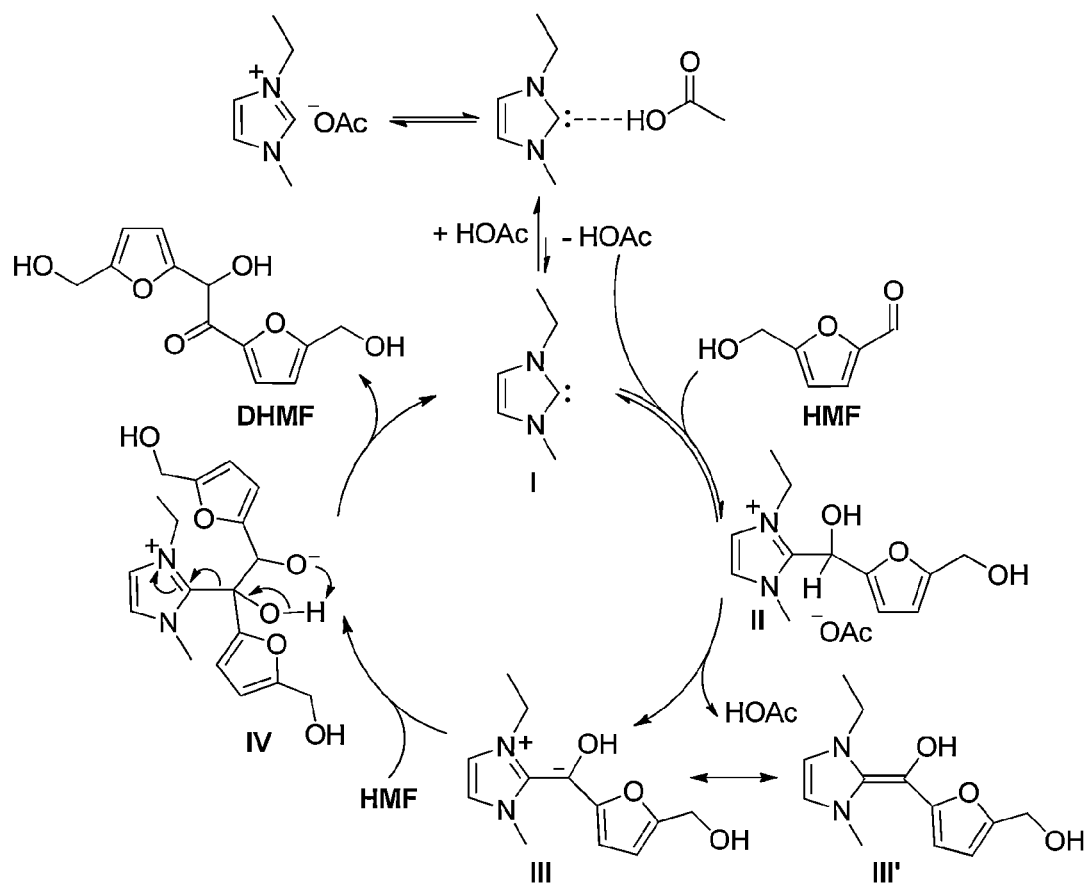
FIG. 3. 3A: Proposed catalytic cycle for umpolung self-condensation of HMF to DHMF by a catalytic IL, [EMIM] OAc. 3B: A schematic representation of the conversion of HMF to DHMF by an N-heterocyclic carbene (NHC).
Figure 3B:
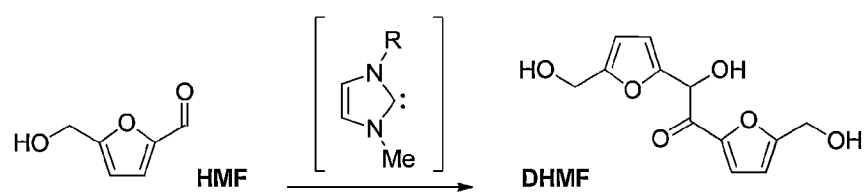

Under elevated temperature, intermediate II is deprotonated by the acetate anion to form a nucleophilic enaminol (III'). Like the Breslow intermediate involved in the benzoin reaction (Breslow, J. Am. Chem. Soc. 1958, 80, 3719), this enaminol is the acyl anion equivalent (III), thus attacking the carbonyl group of a second HMF molecule to form another tetrahedral intermediate (IV). Collapse of this tetrahedral intermediate, via proton transfer and elimination of I, produces DHMF and regenerates the NHC catalyst, thus closing the catalytic cycle (FIG. 3). This proposed overall mechanism explains well the observed catalysis for upgrading of HMF into DHMF by [EMIM]OAc and is consistent with the four lines of evidence presented as follows.

First, previous studies have shown that a small concentration of carbene exists in [EMIM]OAc, which is capable of executing carbene catalysis. To further confirm this point, we replaced [EMIM]OAc with 1-ethyl-2,3-dimethylimidazolium acetate, ([EDMIM]/OAc, in which the acidic proton at C(2) of the imidazolium ring is substituted with the methyl group. As predicted, the carbene catalysis is completely shut down and there is no conversion of HMF into DHMF, thereby supporting the proposed catalyst being the NHC released from [EMIM]OAc.

Second, on the basis of the proposed mechanism, ILs paired with non-basic anions, which are incapable of self-releasing NHCs like [EMIM]OAc, should be ineffective for this carbene catalysis but could be activated, with a strong organic base, to deliver the NHC catalyst and thus effect the same type of carbene catalysis. Indeed, [EMIM]Cl, while itself is ineffective for this catalysis, becomes a highly effective HMF upgrading catalyst system, when treated with DBU (1,8-diazabicyclo[5.4.0]undec-7-ene) which generates the NHC catalyst in situ. Thus, with a 5 mol % catalyst loading, which was controlled by the amount of DBU added, DHMF was obtained in 96% yield (by HPLC) at 80° for 1 hour. Potential co-solvent effects were also examined, showing a minimal effect on DHMF yield.

Figure 4:
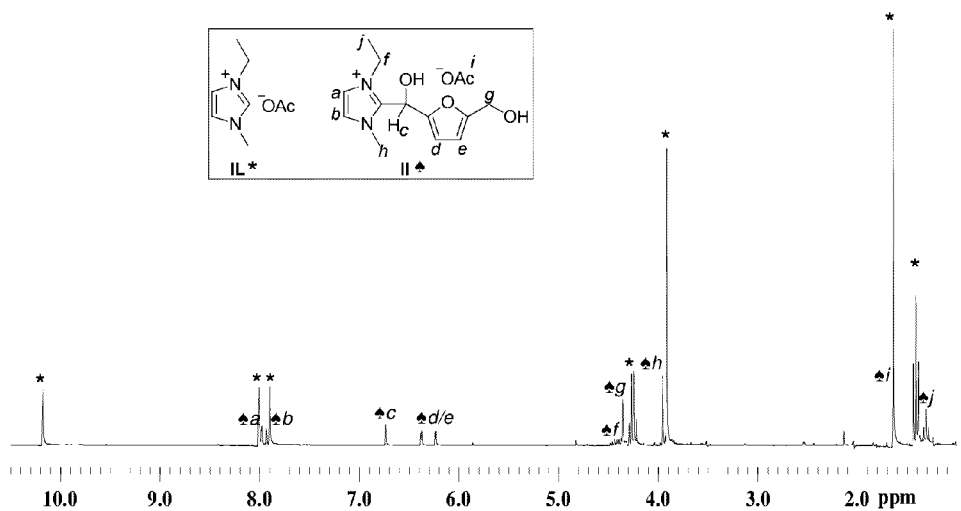
FIG. 4. $^1H$ NMR spectrum of the reaction between HMF and [EMIM]OAc (1:5 molar ratio) at RT for 1.5 hours, showing clean formation of intermediate II in the presence of excess [EMIM]OAc (small unlabeled peaks are for a trace amount of the residual solvents brought from the IL).
Figure 5:
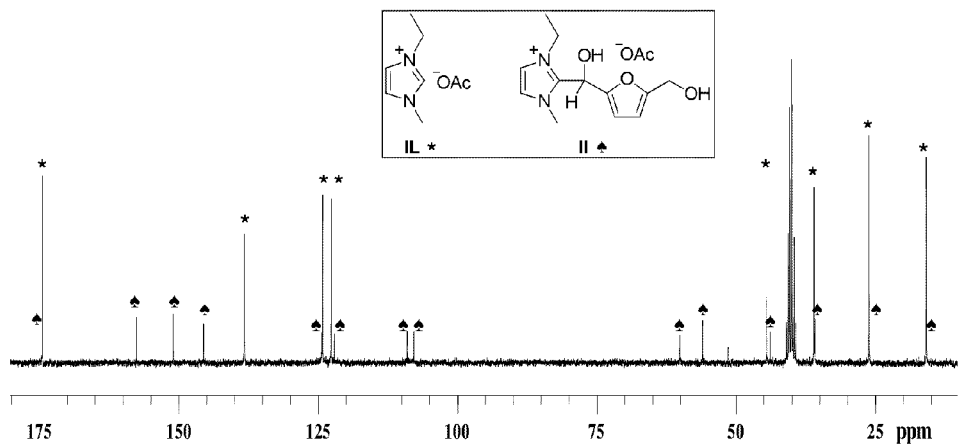
FIG. 5. $^{13}C$ NMR spectrum of the reaction between HMF and [EMIM]OAc (in a 1:5 molar ratio) at RT for 1.5 hours, showing clean formation of intermediate II in the presence of excess [EMIM]OAc (a peak unlabeled is for a trace amount of the residual solvent ($CH_2Cl_2$) brought from the IL).

Third, we obtained direct evidence for the formation of the resting intermediate II through NMR monitoring of the HMF reaction with [EMIM]OAc (1:1 molar ratio) in DMSO-$d_6$ at RT (~22° C.) and 80° C. with hexamethylbenzene as the internal standard. At RT, 17% HMF was consumed immediately upon mixing HMF with [EMIM]OAc, which approximately corresponds to the amount of the NHC catalyst accessible in [EMIM]OAc at this temperature for its reaction with HMF to form intermediate II. This intermediate is not converted into DHMF at RT, even after 24 h. With this valuable information, next we carried out the same reaction at RT but with a 1:5 molar ratio of HMF:[EMIM]OAc to form the intermediate exclusively (i.e., devoid of HMF and DHMF), plus excess [EMIM]OAc; the reaction in this ratio at RT enabled conclusive spectroscopic characterization of intermediate II (FIGS. 4 and 5).

Figure 6:
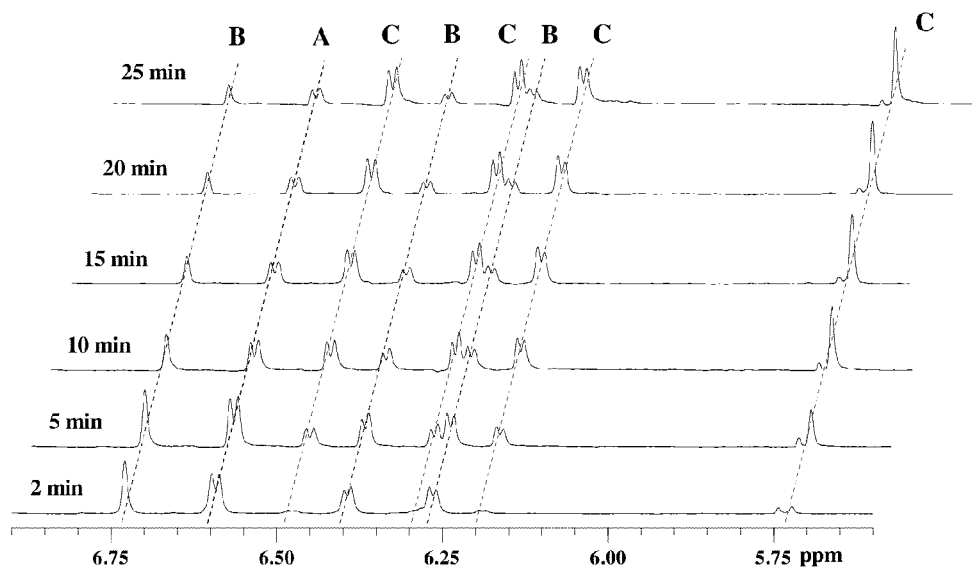
FIG. 6. Comparison of $^1H$ NMR spectra of the reaction between HMF and [EMIM]OAc (1:1 molar ratio) in DMSO-$d_6$ at 80° C. over the initial 25 minute period. This spectral overlay in the most characteristic region shows the gradual decreasing of the intensities (normalized by the $C_6Me_6$ internal standard) of the peaks for HMF (6.59 ppm, "A" line) and intermediate II (6.73, 6.39, 6.26 ppm, "B" lines), with the concomitant increasing of DHMF (6.48, 6.29, 6.19, 5.72 ppm, "C" lines). A small shoulder peak at 5.74 with a constant intensity is the residual solvent ($CH_2Cl_2$) brought from the IL.

At 80° C., on the other hand, FIG. 6 shows that intermediate II is formed instantaneously upon mixing HMF with [EMIM]OAc (1:1 ratio) and, as the reaction proceeds from 2 minutes to 25 minutes, a gradual consumption of this intermediate and HMF, accompanied by concurrent formation of DHMF. Another experiment where heating the intermediate in the absence of HMF led to formation of DHMF indicates that the reaction of NHC I with HMF to form intermediate II is reversible (i.e., release of HMF is needed to further convert II to DHMF at elevated temperature). Overall, these results demonstrate the formation of intermediate II is fast (and reversible), while the II-to-III step is rate-limiting and subsequent steps in the catalytic cycle are also relative fast, as intermediates III and IV were not detectable en route to rapid formation of DHMF.

Fourth, if the small concentration of NHC I present in [EMIM]OAc is the catalyst for self-condensation of HMF to DHMF, then the use of the preformed, discrete NHCs should lead to even more rapid and efficient upgrading of HMF to DHMF. Indeed, with the Enders TPT being the catalyst (5 mol %), near quantitative (98% by NMR) conversion of HMF to DHMF was observed in THF at RT after 24 hours, resulting in a high isolated yield (86%; unoptimized) of DHMF. The rate of the TPT (5 mol %)-catalyzed condensation of HMF can be greatly enhanced at elevated temperature. At 60° C. for 1 hour, 94% DHMF (NMR yield) was achieved within 1 hour, accomplishing a 87% isolated (unoptimized) yield.

The performance of the two Arduengo carbenes, 1,3-di-tert-butylimidazolin-2-ylidene (I$^t$Bu) and 1,3-di-mesityl-butyl-imidazolin-2-ylidene (IMes) (Arduengo et al., J. Am. Chem. Soc. 1994, 116, 6641; Arduengo et al., J. Am. Chem. Soc. 1992, 114, 5530), is drastically different. While IMes is also a highly effective catalyst for upmolung condensation of HMF to DHMF (5 mol % NHC, 93% DHMF by NMR), the more nucleophilic (I$^t$Bu) is completely ineffective. When HMF is mixed with a stoichiometric amount of NHC (TPT, IMes, or I$^t$Bu) at RT, HMF and NHC were completely consumed without producing DHMF, presumably due to the formation of the corresponding adduct. The remarkable activity and efficiency of TPT in this carbene catalysis is presumably related to the fact that TPT is both a good nucleophile and leaving group, the latter of which is essential for closing the catalytic cycle (c.f., FIG. 3).

By the same analogy, the ineffectiveness of I$^t$Bu can be attributed to its strong binding to HMF and being too poor a leaving group to close the cycle. Overall, these results obtained from using the authentic, discrete NHC catalysts as well as the already established reactivity and fundamental steps of such NHCs towards aldehydes (i.e., benzoin reaction) further support the overall umpolung self-condensation of HMF to DHMF mechanism depicted in FIG. 3.

Accordingly, through organocatalysis by the catalytic acetate-based IL [EMIM]OAc, the chloride-based IL [EMIM]Cl in combination with the organic base DBU, or the discrete NHC catalysts TPT and IMes, we have developed a rapid, highly selective and high-yield upgrading of the key biorefining intermediate HMF into DHMF, a potential high-value biorefinery product as an intermediate to kerosene/jet fuel. The reaction time for this HMF upgrading process is within 1 hour under industrially preferred conditions (i.e., ambient atmosphere, or 60-80° C.), and the DHMF selectivity is typically near quantitative and yields are up to 98% (HPLC or NMR) or 87% (unoptimized, isolated yield).

This work has also yielded the carbene catalysis mechanism for this upgrading transformation by the catalytic IL, which has been supported by four lines of evidence presented herein, including the direct identification of the resting intermediate. The technological significance of this work is that, while direct aldol condensation of HMF for its upgrading is not possible (Huber, Chheda, Barrett, and Dumesic, *Science* 2005, 308, 1446), the direct umpolung self-condensation of HMF for its upgrading into DHMF is highly facile, which is made possible by organocatalysis. Additionally, as many efficient catalyst systems have been developed for conversion of plant biomass resources (glucose or cellulose) into HMF (see, for example, Zhang et al., *Energy & Fuels* 2010, 24, 2410), it is now possible to convert such nonfood biomass directly into DHMF via a two-step process. Indeed, our results show the feasibility of transforming glucose directly into DHMF in a step-wise fashion, with the first step converting glucose into HMF by metal catalysis, followed by extraction of HMF and subsequent carbene catalysis.

Coupling Reactions and Product Analysis.

Typical Procedure for Studying HMF Degradation in [EMIM]OAc and the Corresponding Results.

Figure 7:
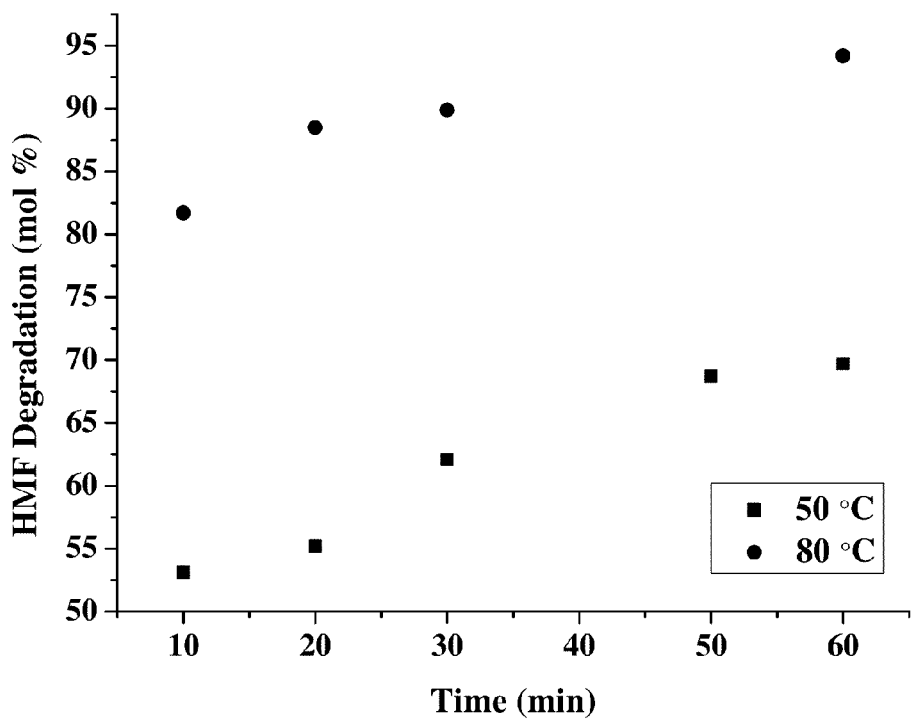
FIG. 7. Graphical profiles of HMF degradation (mol %) in [EMIM]OAc (1:1 molar ratio) vs. time at two different temperatures (50° C. and 80° C.), monitored by HPLC.

HMF (0.10 g, 0.79 mmol) was mixed with [EMIM]OAc (0.14 g, equimolar to HMF) in a 5 mL vial. The vial was sealed and heated at 80° C. for a period of time in a temperature-controlled orbit shaker (300 RPM). The reaction was quenched with ice-water and diluted with a known amount of deionized water. HMF was quantified with calibration curves generated from the commercially available standard in water (Liu et al., *Appl. Catal. A: Gen.* 2012, 435/436, 78). A typical HPLC chromatogram of the reaction product is shown in FIG. 1. The results of HMF degradation in [EMIM]OAc monitored by HPLC are summarized in Table 1-1 and FIG. 7, which showed that [EMIM]OAc rapidly degrades HMF at 80° C.; for instance, HMF degraded by 81.7 and 94.2 mol % after only 10 and 60 min, respectively.

TABLE 1-1

Data profiles (by HPLC) for HMF degradation in [EMIM]OAc.

| temperature (° C.) | time (minutes) | HMF degradation (mol %) |
|---|---|---|
| 50 | 10 | 53.1 |
|  | 20 | 55.2 |
|  | 30 | 62.1 |
|  | 50 | 68.7 |
|  | 60 | 69.7 |

TABLE 1-1-continued

Data profiles (by HPLC) for HMF degradation in [EMIM]OAc.

| temperature (° C.) | time (minutes) | HMF degradation (mol %) |
|---|---|---|
| 80 | 10 | 81.7 |
|  | 20 | 88.5 |
|  | 30 | 89.9 |
|  | 60 | 94.2 |

For investigation of the HMF degradation kinetics in [EMIM]OAc, HMF (40.0 mg, 0.32 mmol) and hexamethylbenzene (2.0 mg, 0.012 mmol) were fully dissolved in 0.5 mL DMSO-$d_6$, followed by addition of [EMIM]OAc (1 equiv relative to HMF) in 0.5 mL DMSO-$d_6$. The mixture was transferred into a J. Young-type NMR tube and sealed with the Teflon valve. The mixture was heated to 80° C. on an NMR spectrometer and the reaction was followed by taking $^1$H NMR spectra of the reaction mixture at predetermined time intervals. The results of HMF degradation in [EMIM]OAc monitored by NMR are summarized in FIG. 8 (profiles of HMF degradation as a function of time) and FIG. 9 (the first-order plot of HMF degradation for the initial time period).

Isolation and Characterization of DHMF Produced from HMF Degradation in [EMIM]OAc.

As FIG. 1 shows, the HPLC chromatogram of the reaction mixture from the incomplete HMF degradation in [EMIM]OAc exhibited a peak at 3.72 minutes for the unreacted HMF, plus a large peak at 5.15 minutes for a new compound formed during HMF degradation in [EMIM]OAc. To separate the new compound from the reaction mixture after the reaction at 80° C. for 30 minute, 1 mL water was added to fully dissolve the mixture, after which 2 mL ethyl acetate (EtOAc) was added for extraction. The upper layer (EtOAc phase) was collected and the extraction was repeated four times. The new compound was obtained as a light yellow powder (50% isolated yield based on HMF) after purification by the silica gel column chromatography (eluent: EtOAc/hexane/methanol=8/2/1) and vacuum drying.

Figure 10:
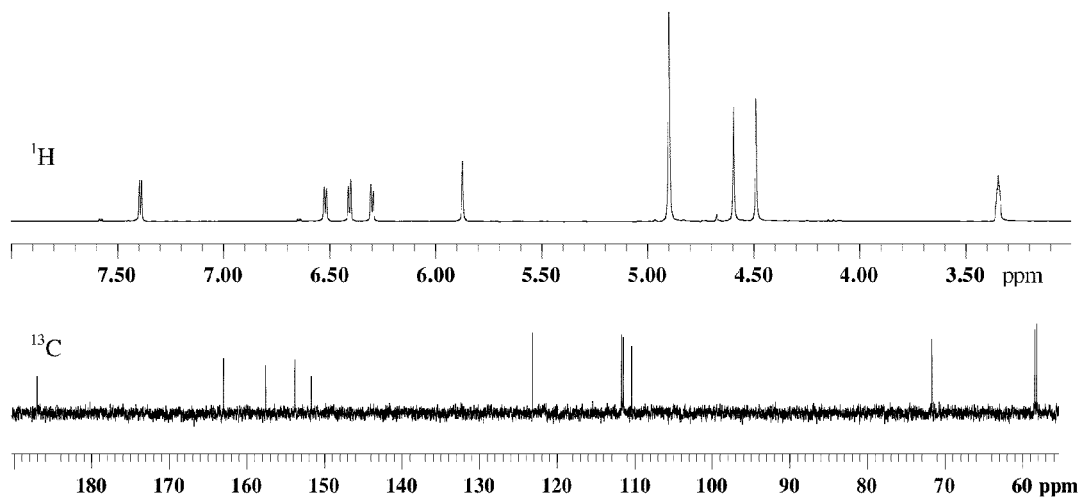
FIG. 10. $^1H$ and $^{13}C$ NMR spectra of DHMF in methanol-$d_4$. Note that peaks at 3.31 ppm and 4.87 ppm on the $^1H$ NMR spectrum are for the NMR solvent residual and $H_2O$ signals, respectively. The methanol residual signal at 49.86 ppm on the $^{13}C$ NMR spectrum is not shown in the expansion region of the spectrum illustrated in the figure.

The degradation product (new compound) was identified as 5,5'-di(hydroxymethyl)furoin (DHMF), as clearly shown by its $^1$H and $^{13}$C NMR spectra (FIG. 10). $^1$H NMR (CD$_3$OD): δ 7.39 (d, $J_{H-H}$=3.6 Hz, 1H, furan ring proton), 6.52 (d, $J_{H-H}$=3.6 Hz, 1H, furan ring proton), 6.40 (d, $J_{H-H}$=3.3 Hz, 1H, furan ring proton), 6.30 (d, $J_{H-H}$=3.3 Hz, 1H, furan ring proton), 5.87 (s, 1H, CHOH), 4.60 (s, 2H, CH$_2$OH), 4.49 (s, 2H, CH$_2$OH). $^{13}$C NMR (CD$_3$OD): δ 187 (C=O), 163, 158, 154, 152, 123, 112, 111, 110 (a total of 8 resonances for the furan ring carbons), 71.7 (CHOH), 58.4 (CH$_2$OH), 58.2 (CH$_2$OH). M.p.=124-125° C.; HRMS calculated for C$_{12}$H$_{11}$O$_6$ [M–H]$^-$: 251.0556; found: 251.0561.

The DHMF purified by the silica gel column chromatography was recrystallized by slow diffusion of hexanes into a methanol solution of DHMF at room temperature over 7 d, affording colorless single crystals suitable for X-ray diffraction analysis. Single crystals were quickly covered with a layer of Paratone-N oil (Exxon, dried and degassed at 120° C./10$^{-6}$ Torr for 24 hours) after decanting the mother liquor. A crystal was then mounted onto a thin glass fiber and transferred into the cold nitrogen stream of a Bruker SMART CCD diffractometer. The structure was solved by direct methods and refined using the Bruker SHELXTL program library (*SHELXTL*, Version 6.12; Bruker Analytical X-ray Solutions: Madison, Wis., 2001).

The structure was refined by full-matrix least-squares on $F^2$ for all reflections. All non-hydrogen atoms were refined with anisotropic displacement parameters, whereas hydrogen atoms were included in the structure factor calculations at idealized positions. The solved structure showed two independent molecules with minor structural differences in the unit cell (FIG. 2). Selected crystallographic data for DHMF: $C_{24}H_{24}O_{12}$, Orthorhombic, space group $Pna2_1$, a=23.5497(17) Å, b=5.9975(4) Å, c=15.8768(10) Å, α=90°, β=90°, γ=90°, V=2242.4(3) Å$^3$, Z=4, $D_{calcd}$=1.494 Mg/m$^3$, GOF=1.040, R1=0.0524 [I>2σ(I)], wR2=0.1309. CCDC-887451 contains the supplementary crystallographic data for this paper. These data can be obtained free of charge from The Cambridge Crystallographic Data Centre via www.ccdc.cam.ac.uk/data_request/cif.

Figure 8:
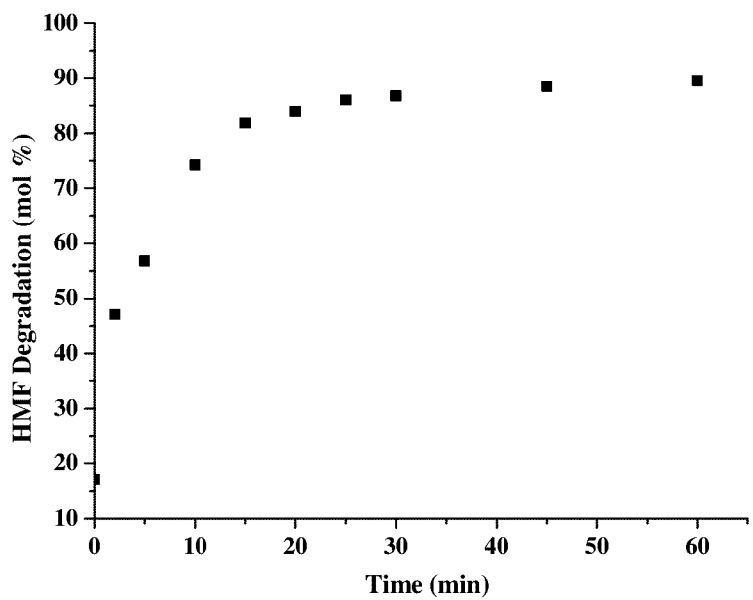
FIG. 8. Profile (by NMR) of HMF degradation in [EMIM] OAc (1:1 molar ratio) at 80° C., showing rapid HMF degradation by 17.1% at 0 min, 47.1% at 2 m, 56.8% at 5 m, 74.2% at 10 m, 81.9% at 15 min, 84.0% at 20 m, 86.1% at 25 m, 88.5 at 45 m, and 89.6% at 60 min.
Figure 9:
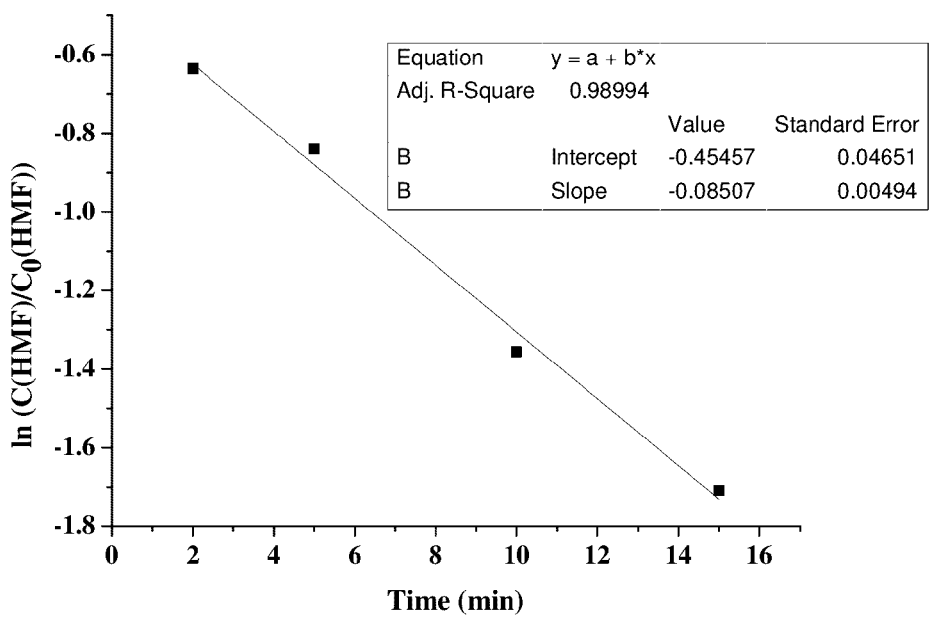
FIG. 9. The first-order plot of the HMF degradation in [EMIM]OAc (1:1 molar ratio) at 80° C. for the initial time period (2-15 minutes).
Figure 11:
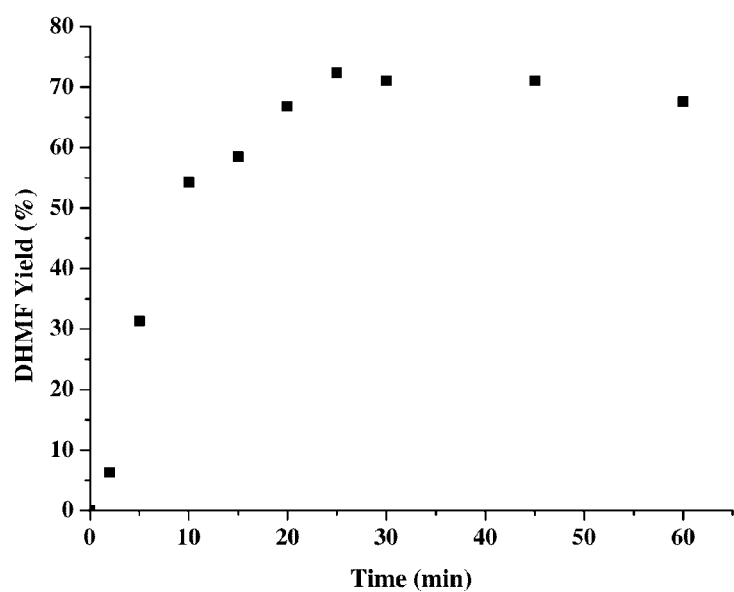
FIG. 11. DHMF yield (by NMR) as a function of HMF degradation time in [EMIM]OAc (1:1 molar ratio) at 80° C.

The identification as well as spectroscopic and structural characterizations of the HMF degradation product (DHMF) allowed for monitoring of DHMF formation and HMF degradation simultaneously by NMR (DMSO-d$_6$, 80° C., hexamethylbenzene as the internal standard). The results were summarized in Table 1-2, FIG. 8, and FIG. 11, showing that a high yield of 72.4% was achieved at 86.1% HMF conversion (degradation) after 25 minutes.

TABLE 1-2

Data (by NMR) for HMF degradation and DHMF yield in [EMIM]OAc at 80° C.

| time (min) | HMF degradation (mol %) | DHMF yield (mol %) |
|---|---|---|
| 0 | 17.1 | 0 |
| 2 | 47.1 | 6.3 |
| 5 | 56.8 | 31.3 |
| 10 | 74.2 | 54.3 |
| 15 | 81.9 | 58.5 |
| 20 | 84.0 | 66.9 |
| 25 | 86.1 | 72.4 |
| 30 | 86.8 | 71.0 |
| 45 | 88.5 | 71.0 |
| 60 | 89.6 | 67.6 |

Identification of Intermediate II from the Reaction of HMF with [EMIM]OAc.

The 1:1 reaction of HMF with [EMIM]OAc at RT was monitored by NMR (DMSO-d$_6$) in a J. Young-type NMR tube using hexamethylbenzene as the internal standard. This study showed that 17% HMF was consumed immediately upon mixing HMF with [EMIM]OAc at RT, which approximately corresponds to the amount of the NHC catalyst accessible in [EMIM]OAc at this temperature for its reaction with HMF to form intermediate II. This intermediate is not converted into DHMF at RT, even after 24 hours, and the $^1$H NMR remained the same from the beginning of the reaction up to 24 hours at RT.

To aid analysis of the spectra of the in situ reactions, the chemical shifts of the four species involved in the reaction of HMF with [EMIM]OAc were summarized as follows. All chemical shifts were reported in DMSO-d$_6$, and the NMR solvent residual signal was referenced at 2.54 ppm (not 2.50 ppm), based on the chemical shift of the hexamethylbenzene internal standard set at 2.15 ppm.

$^1$H NMR for HMF (known compound): δ 9.56 (s, 1H, CHO), 7.51, 6.59 (d, 2H, furan ring H), 4.54 (s, 2H, CH$_2$OH).

$^1$H NMR for [EMIM]OAc (known compound): δ 9.60 (s, 1H, NCHN), 7.84, 7.76 (d, 2H, imidazolium ring H), 4.24 (q, 2H, NCH$_2$CH$_3$), 3.89 (s, 3H, NCH$_3$), 1.65 (s, 3H, OAc), 1.44 (t, 3H, NCH$_2$CH$_3$).

Figure 12:
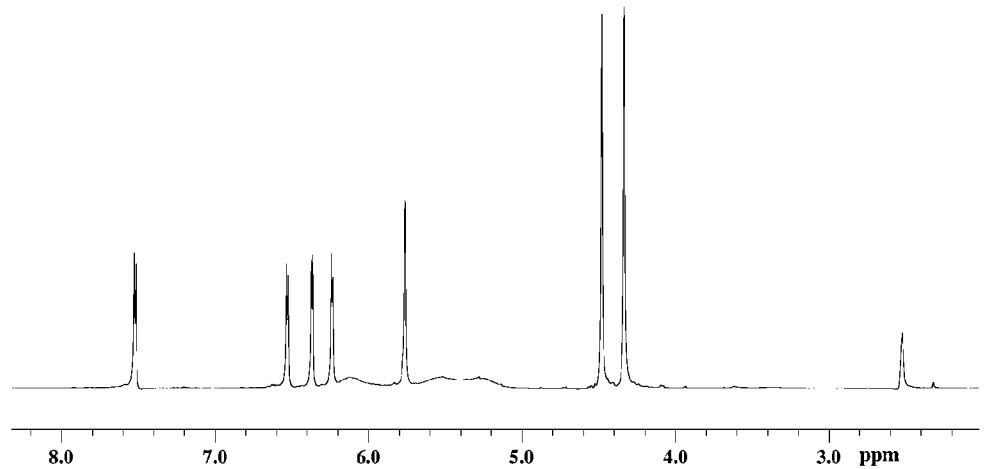
FIG. 12. $^1H$ NMR (DMSO-$d_6$) of DHMF derived from umpolung condensation of HMF by TPT. Note the three broad peaks centered at ~5.3 ppm, 5.5 ppm, and 6.1 ppm, not appeared in the $^1H$ NMR taken in methanol-$d_4$ (FIG. 10), are for three types of the OH groups present in DHMF, and the peak at 2.54 ppm is from the residual solvent signal.

$^1$H NMR for DHMF (new compound, see FIG. 10 in methanol-d$_4$ and FIG. 12 in DMSO-d$_6$): δ 7.54, 6.54, 6.38, 6.25 (d, 4H, furan ring H), 5.78 (s, 1H, CHOH), 4.50 (s, 2H, CH$_2$OH), 4.35 (s, 2H, CH$_2$OH).

$^1$H NMR for Intermediate II (new compound, see FIGS. 4 and 5): δ 7.98 (d, $J_{H-H}$=2.1 Hz, imidazol ring H), 7.93 (d, $J_{H-H}$=1.8 Hz, 1H, imidazol ring proton), 6.74 (s, 1H, CH—OH), 6.38 (d, $J_{H-H}$=3.3, 1H, furan ring H), 6.24 (d, $J_{H-H}$=3.0 Hz, 1H, furan ring H), 4.41 (m, 2H, NCH$_2$CH$_3$), 4.36 (s, 2H, CH$_2$OH), 3.96 (s, 3H, NCH$_3$), 1.64 (s, 3H, OAc), 1.31 (t, $J_{H-H}$=7.2 Hz, 3H, NCH$_2$CH$_3$). $^{13}$C NMR: δ 175 (C=O), 158 (NCN), 151, 146, 109, 108 (4 resonances for the furan ring), 125, 122 (2 resonances for the imidazol ring), 60.4 (CH—OH), 56.3 (CH$_2$OH), 44.2 (NCH$_2$CH$_3$), 36.2 (NCH$_3$), 26.5 (O=C—CH$_3$), 16.3 (NCH$_2$CH$_3$).

Solvent-Free Umpolung Procedures for Coupling of Furaldehydes.

Umpolung reactions catalyzed by TPT were carried out under solvent-free (neat) conditions. Furfural (2.5 g, 26 mmol) was added in a 20 mL vial, to which TPT (71 mg, 0.26 mmol, 1.0 mol % to furfural) was added. The resulting mixture was stirred for 1 hour, after which the solidified product was crushed and washed with hexanes. Furoin (2.2 g, 89% yield) was obtained as yellow powder after filtration and vacuum drying. Using the same procedure, 5,5'-dimethylfuroin was synthesized from MF in 94% isolated yield.

For the synthesis of 5,5'-di(hydroxymethyl)furoin (DHMF), HMF (2.5 g, 20 mmol) was premixed with TPT (55 mg, 0.20 mmol, 1.0 mol % relative to HMF) in a 20 mL vial. The vial was sealed and heated at 60° C. for 1 hour by a temperature-controlled orbit shaker (300 rpm). After the reaction, the solidified product was crushed and washed with toluene to remove the residual TPT catalyst. DHMF (2.4 g, 95% yield) was obtained as white powder after filtration and vacuum drying.

Stoichiometric Reaction of HMF and N-heterocyclic Carbene (NHC).

Figure 13:
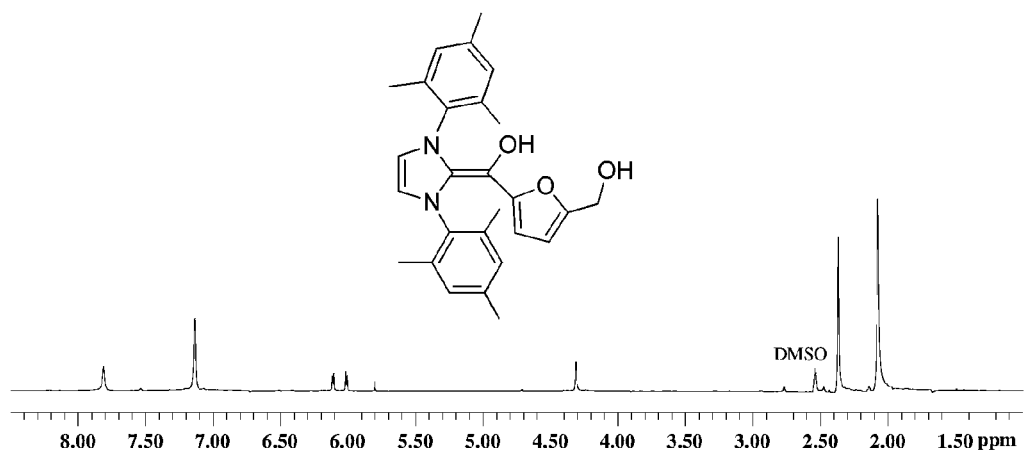
FIG. 13. $^1H$ NMR spectrum of the resulting enaminol (the Breslow intermediate) derived from the reaction of HMF and IMes.

HMF (20 mg, 0.16 mmol) was dissolved into 0.5 mL DMSO-d$_6$ and transferred into a J. Young-type NMR tube, to which a stoichiometric amount of IMes (48 mg, 0.16 mmol) in 0.5 mL DMSO-d$_6$ was added and fully mixed. After 30 minutes at RT, the clean formation of the Breslow enaminol, the Breslow intermediate involved in the benzoin reaction, was indicated by $^1$H NMR spectrum (FIG. 13). $^1$H NMR (DMSO-d$_6$): δ 7.81 (s, 2H, imidazole ring protons), 7.14 (s, 4H, benzene ring protons), 6.11 (d, $J_{H-H}$=3.0 Hz, 1H, furan ring proton), 6.01 (d, $J_{H-H}$=3.3 Hz, 1H, furan ring proton), 4.31 (s, 2H, CH$_2$OH), 2.37 (s, 6H, p-CH$_3$), 2.08 (s, 12H, o-CH$_3$).

Typical Procedure for Studying Umpolung Condensation of HMF into DHMF by NHCs and the Corresponding Results.

In a typical procedure, HMF (115 mg, 0.91 mmol) was fully dissolved in 5 mL THF, followed by addition of TPT (5 mol %) in 0.5 mL THF. The resulting solution was stirred at room temperature, and aliquots were taken from time to time and dried under vacuum for analysis by $^1$H NMR in DMSO-d$_6$. To isolate DHMF from the HMF self-condensation catalyzed by TPT, the reaction mixture was stirred at room temperature for 24 hours and then concentrated, followed by addition of toluene to precipitate the product DHMF. DHMF (99 mg, 86% yield) was obtained as white solid after filtration and vacuum drying. $^1$H NMR in DMSO-d$_6$ of the product (FIG. 12) confirmed the clean formation of DHMF. The same reaction was repeated at 60° C. for 1 hour, affording DHMF in 87% isolated yield.

Table 1-3 summarizes selected results of the DHMF yield under various conditions achieved by three NHC catalysts, TPT, I'Bu, and IMes. The most efficient catalyst in this series is TPT, which converted HMF to DHMF in 98% yield (by NMR, or 86% isolated yield) with a low catalyst loading of 5 mol % at RT after 24 hours. The rate of HMF condensation can be greatly enhanced when carrying out the reaction at 60° C., which achieved 93.6% DHMF yield after 1 hour, compared to 37.5% DHMF yield at RT after 3 hours. In comparison, IMes is somewhat less effective than TPT, but I'Bu is completely ineffective. However, when a stoichiometric amount of NHC (relative to HMF) was used at RT, in all cases HMF was completely consumed without forming DHMF.

TABLE 1-3

Results of HMF self-condensation to DHMF catalyzed by NHCs.

| NHC | NHC loading (mol %) | temperature (° C.) | time (h) | DHMF yield (NMR) (%) | DHMF yield (isolated) (%) |
|---|---|---|---|---|---|
| I'Bu | 5 | 25 | 24 | 0 | 0 |
|  | 100 | 25 | 24 | 0 | 0 |
| IMes | 5 | 25 | 24 | 92.9 | n.d. |
|  | 100 | 25 | 24 | 0 | 0 |
| TPT | 5 | 25 | 24 | 98.0 | 86.2 |
|  | 100 | 25 | 24 | trace | n.d. |
|  | 5 | 60 | 1 | 93.6 | 87.1 |

Solvent: THF.
n.d. = not determined.

While [EMIM]Cl itself is ineffective for this catalysis, the [EMIM]Cl+DBU (5 mol %) system, which generates the NHC catalyst in situ, is highly effective for HMF upgrading. The NHC catalyst loading is conveniently controlled by the amount of DBU added to the reaction mixture. Specifically, HMF was premixed with [EMIM]Cl (1 equiv) and DBU (5 mol %) and heated at 80° C. for 1 hour, DHMF was formed in 96.4% yield (by HPLC). Potential co-solvent effects were also examined, showing a minimal effect on the DHMF yield; thus, addition of the THF co-solvent gave a DHMF yield of 96.7%, while the yield was 93.8% when employing DMF as a co-solvent.

Example 2

Upgrading Biomass Furaldehydes to Value-Added Chemicals, Oxygenated Diesel, and Premium Alkane Fuels Recognized as a key biorefining building block and the biomass platform chemical, 5-hydroxymethylfurfural (HMF) has been studied extensively as part of major efforts in developing technologically and economically feasible routes for converting nonfood lignocellulosic biomass into feedstock chemicals, sustainable materials, and liquid fuels. Since the important discovery of the $CrCl_2$/ionic liquid (IL) catalyst system for effective conversion of the cellulosic glucose to HMF (Zhao et al., Science 2007, 316, 1597), a large number of other metal or non-metal catalyst systems have been developed to promote effective conversion of glucose or directly cellulose into HMF (for example, see Liu and Chen, Biomass & Bioenergy, 2013, 48, 181-190). In contrast, research on the upgrading of HMF or related furaldehydes into higher molecular-weight and energy-density kerosene ($C_8$ to $C_{16}$) or diesel (up to $C_{22}$) intermediates or fuels is scarce and thus much needed.

Considering the fact that HMF cannot undergo self-aldol condensation due to lack of an α-hydrogen, Dumesic and co-workers utilized cross-aldol condensation of HMF with enolizable organic compounds such as acetone in the presence of an alkaline catalyst, followed by dehydration/hydrogenation processes, to upgrade HMF into $C_9$ to $C_{15}$ liquid alkane fuels (Scheme 2-1, route A) (Huber et al., Science, 2005, 308, 1446). Recently, Corma and co-workers developed hydroxyalkylation of 2-methylfuran to perform trimerization in the presence of an acid catalyst, the product of which is subject to high-temperature hydrodeoxygenation (HDO) to produce high-cetane number 6-alkylundecanes (Corma et al., Angew. Chem. Int. Ed. 2011, 50, 2375). HMF can be used to replace one of the 2-methylfuran molecules in the trimerization step (Scheme 2-1, route B). Most recently, Bell and co-workers reported acid-catalyzed etherification and reductive etherification of HMF into 5-(alkoxymethyl)furfurals and 2,5-bis(alkoxymethyl)furans as potential oxygenated biodiesel candidates (Scheme 2-1, route C) (Balakrishnan et al., Green Chem. 2012, 14, 1626). This direct HMF etherification route offers an alternative for producing usable diesel-range fuels to the etherification of the chloride derivative of HMF, 5-(chloromethyl)furfural, with alcohol (Mascal and Nikitin, Green Chem. 2010, 12, 370).

Scheme 2-1. Various routes to upgrade HMF into kerosene or diesel intermediates and fuels.

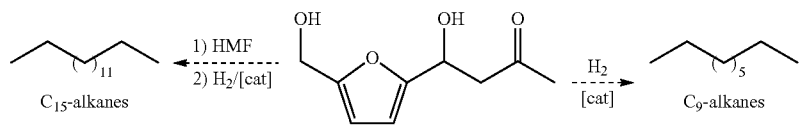

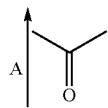

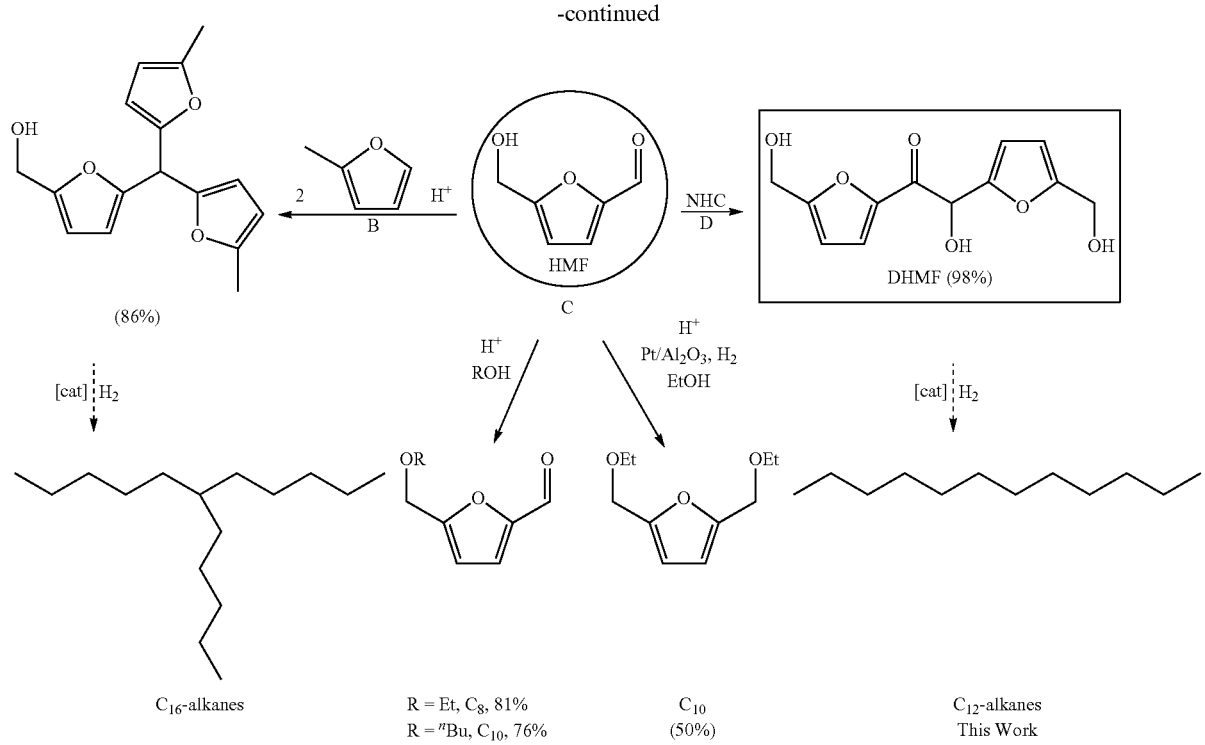

Recent research on hydrodeoxygenation (HDO) has focused on the development of bifunctional catalysts for upgrading lignin-derived pyrolysis oils (phenols, guiaiacols and syringols, etc.) into hydrocarbons. Water can be used as a suitable solvent for HDO, allowing for spontaneous separation of hydrocarbons during the reaction. Supported catalysts such as Ni/HZSM-5, Pd/C+$H_3PO_4$ and Pd/C+HZSM-5 can achieve high to quantitative yield of cycloalkanes from phenols under 5 MPa $H_2$ at 250° C. within 2 hours (Zhao and Lercher, *Angew. Chem. Int. Ed.* 2012, 51, 5935). However, for furan compounds derived from cellulosic biomass, HDO products are complicated by furan-ring opening, carbon chain fragmentation, rearrangement, and cyclization, rendering a wide distribution of hydrocarbons.

Using conditions similar to those employed for the HDO of the lignin-derived pyrolysis oils, the HDO of furfural gave tetrahydropyran in 36% yield besides pentane. For the HDO of 5-methylfuran trimer (5,5-bisylvyl-2-pentanone) by Pt/C and Pt/$TiO_2$ under 5 MPa $H_2$ and 400° C., 96% oily products were classified as $C_9$ to $C_{16}$ hydrocarbons (linear, branched, monocyclic, and bicyclic). In a two-step HDO of furoin consisting of hydrogenation by Pd/$Al_2O_3$ to render the substrate water soluble and the subsequent HDO process with Pt/$SiO_2$—$Al_2O_3$, Dumesic et al. obtained a wide distribution of alkanes, with 34% $C_{10}$ selectivity (*Science*, 2005, 308, 1446). The HDO of the reductive Pinacol coupling products of furfural and 5-methylfurfural (MF) by Pt/C and solid acid TaO$PO_4$ afforded high yield of alkanes (Huang et al., *RSC Advances*, 2012, 2, 11211). Alternatively, opening the furan rings first under mild conditions (which is applicable only to certain types of furan rings), followed by HDO, could potentially produce alkanes more selectively.

Direct coupling of two HMF molecules would provide a sulfur-free $C_{12}$ jet/kerosene fuel intermediate, which could be catalytically reformed into liquid fuels. Herein we report the selective and quantitative coupling of HMF to 5,5'-di (hydroxymethyl)furoin (DHMF) under solvent-free conditions using 1 mol % of an organic N-heterocyclic carbene (NHC) catalyst and subsequent transformations of DHMF into oxygenated diesel fuels through hydrogenation, etherification or esterification, as well as high quality kerosene/jet fuels through a highly selective HDO process that produces nearly quantitative linear hydrocarbons (96% $C_{10-12}$ linear alkanes) in the organic phase (Scheme 2-1, route D).

As discussed above in Examples 1 and 2, through the NHC-catalyzed umpolung benzoin condensation mechanism in the presence of a catalytic acetate IL, 1-ethyl-3-methylimidazolium acetate, or a discrete NHC catalyst (5 mol % 1,3,4-triphenyl-4,5-dihydro-1H-1,2,4-triazol-5-ylidene, TPT), at 60° C. in THF for 1 h, HMF can be selectively self-coupled into DHMF, a promising new $C_{12}$ kerosene/jet fuel intermediate (Liu et al., *Green Chem.* 2012, 14, 2738-2746). This coupling reaction is unique to the organically catalyzed umpolung reaction, as other types of coupling reactions, such as reductive Pinacol coupling, did not work for HMF.

As described in this example, we found that this catalytic coupling reaction can be carried out in the absence of any solvent, even though both HMF and the NHC catalyst are solids (Scheme 2-2). With a TPT loading of 1 mol %, quantitative HMF conversion was observed at 60° C. after 1 hour and DHMF was formed quantitatively (by NMR) with a high isolated yield of 95%. Using a lower catalyst loading of 0.5 mol %, an isolated yield of 87% can still be achieved. Likewise, furfural and 5-methylfurfural (MF) can also be coupled using 1 mol % TPT, even at room temperature, into 1,2-di(furan-2-yl)-2-hydroxyethanone (furoin) and 5,5'-dimethylfuroin in 89% and 94% isolated yields, respectively.

Scheme 2-2. Solvent-free self-condensation of furaldehydes to furoins catalyzed by an NHC catalyst and depicted catalytic cycle for the umpolung condensation of HMF to DHMF.

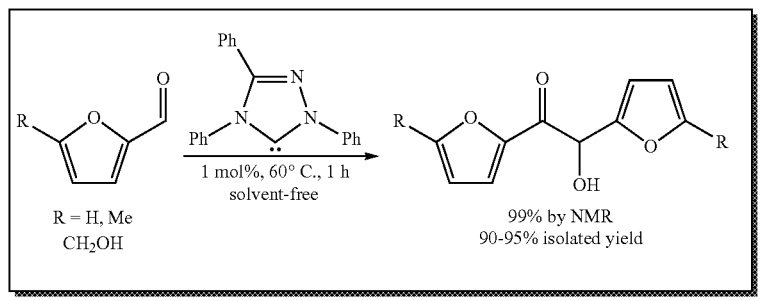

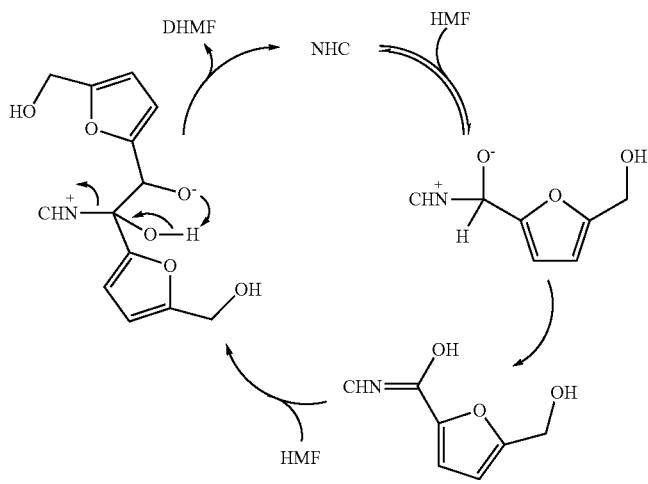

Umpolung of aldehydes catalyzed by NHCs is proposed to proceed through the nucleophilic enaminol or the Breslow intermediate involved in the benzoin reaction. Indeed, we observed the formation of such an intermediate through the stoichiometric reaction of HMF and 1,3-bis(2,4,6-trimethylphenyl)-1,3-dihydro-2H-imidazol-2-ylidene (IMes) in DMSO-$d_6$ at ambient temperature (FIG. 13). This enaminol is the acyl anion equivalent, thus attacking the carbonyl group of a second HMF molecule to form another tetrahedral intermediate. Collapse of this tetrahedral intermediate, via proton transfer and elimination of the NHC, produces DHMF and regenerates the NHC catalyst, thus closing the catalytic cycle and leading to the catalytic formation of the coupling product DHMF (Scheme 2-2).

As the self-condensation products of the three furaldehydes are solids, three routes were investigated to convert them into liquids as potential jet or diesel fuels. We first examined the hydrogenation route to convert the furoins into their saturated derivatives using the recyclable Pd/C catalyst. Under modest hydrogenation conditions (2.7 MPa $H_2$ and 90° C.) in the presence of 10 mol % Pd/C, all three furoins were successfully converted into liquids (Scheme 2-3).

Scheme 2-3. Hydrogenation of furoins and etherification and esterififcation of DHMF into oxygenated liquid diesel candidates.

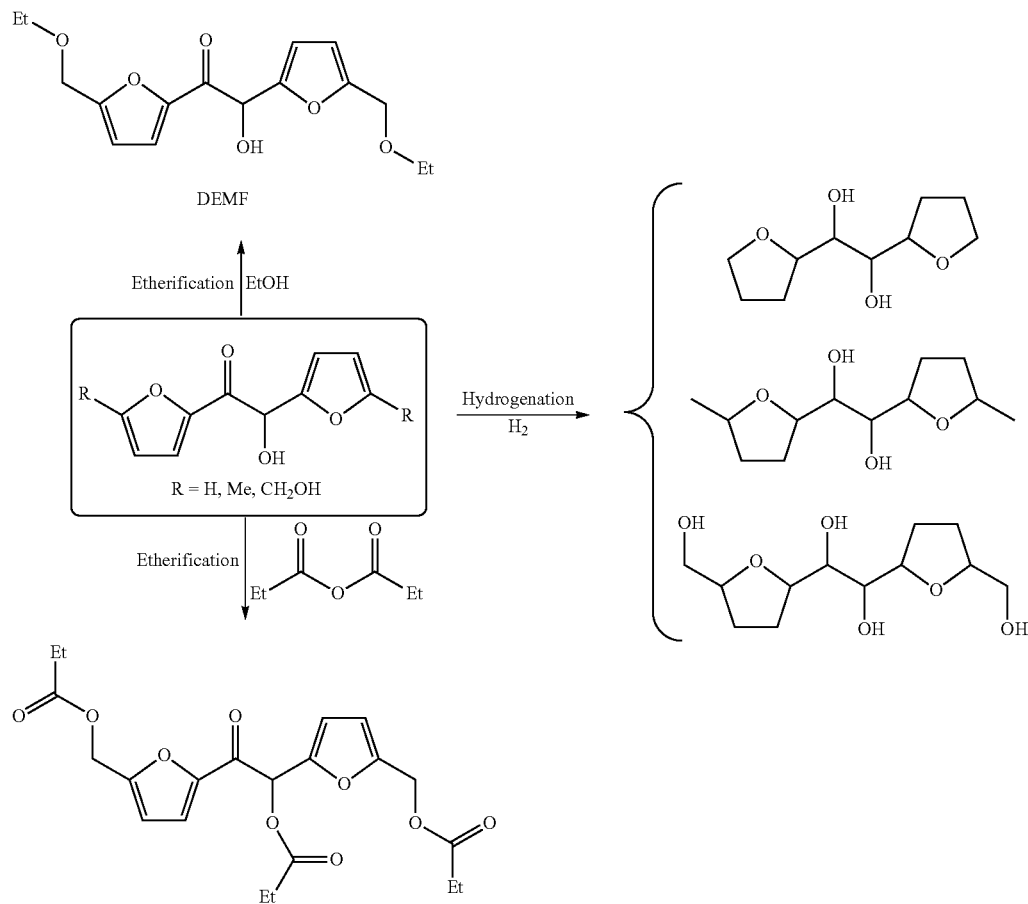

The liquids were not simply fully hydrogenated products, but accompanied with some hydrogenolysis products, as suggested by the elemental results that showed C and H contents were higher than the theoretical values of the fully hydrogenated products (Table 2-1). Heating values of the hydrogenated products from furoin and 5,5'-dimethylfuroin were measured to be 32.7 and 33.3 MJ/kg, respectively, which are noticeably higher than that for ethanol (28.6 MJ/kg), approaching to the value for dimethylfuran (33.7 MJ/kg). These results indicated the potential use of furoin and 5,5'-dimethylfuroin as oxygenated liquid fuels after simple hydrogenation.

TABLE 2-1

Results of elemental analysis of hydrogenated coupling products.

| | Before Hydrogenation | | After Hydrogenation | | | |
| --- | --- | --- | --- | --- | --- | --- |
| | | | Theoretical Value | | Experimental Value | |
| furoins | C (%) | H (%) | C (%) | H (%) | C (%) | H (%) |
| furoin | 62.5 | 4.2 | 59.4 | 8.9 | 65.6 | 11.0 |
| 5,5'-dimethyl-furoin | 65.4 | 5.4 | 62.6 | 9.6 | 67.1 | 10.7 |
| DHMF | 57.1 | 4.8 | 55.0 | 8.4 | 60.5 | 10.1 |

Next, following the procedures established for etherification of HMF with alcohols to form 5-(alkoxymethyl)furfurals (Balakrishnan et al., Green Chem. 2012, 14, 1626) and acetylation of the hydrogenated acetal derived from furfural and glycerol, we investigated etherification and esterification routes to convert DHMF into its corresponding ether with ethanol and ester with propionic anhydride. Indeed, HMF, employed as a control run, was quantitatively converted to 5-ethoxymethylfurfural by NMR [$^1$H NMR (CDCl$_3$): δ 9.64 (s, 1H, CHO), 7.24, 6.55 (d, 2H, furan ring H), 4.56 (s, 2H, CH$_2$OH), 3.62 (q, 2H, CH$_2$CH$_3$), 1.28 (t, 3H, CH$_2$CH$_3$)] in excess of ethanol at 75° C. for 24 hours with solid acid catalyst Dowex G-26 (H-form) resin. Under similar conditions, DHMF was also quantitatively converted to the corresponding liquid ether, 5,5'-di(ethoxymethyl)furoin (DEMF), with the secondary alcohol remaining intact (further discussed below). On the other hand, esterification of DHMF using excess propionic anhydride esterified all three hydroxyl groups, thus forming DHMF-tripropionic ester (Scheme 2-3). Hence, both the etherification and esterification routes can serve as alternative strategies for liquefying DHMF into diesel fuels.

The third route utilized the HDO process through metal-acid tandem catalysis. The overall HDO process of DHMF to linear alkanes (Scheme 2-1) can proceed through metal-catalyzed hydrogenation to give the saturated polyol, acid-catalyzed ring-opening/hydrolysis of furan rings in aqueous solution to yield a straight-chain polyol, and acid-catalyzed dehydration, followed by metal-catalyzed hydrogenation to afford the final saturated linear $C_{12}$ alkane, n-dodecane, ideally with minimum fragmentation, branching, or cyclization. This overall picture calls for a bifunctional catalyst with both metal and acid sites (e.g., noble metal on acidic support, Pt/CsH$_2$PW$_{12}$O$_{40}$ (Alotaibi et al., *Chem. Commun.* 2012, 48, 7194; Tian et al., *Chem. Eng. Technol.* 2011, 34, 482)) to promote this HDO process, comprising hydrogenation-ring-opening/hydrolysis-dehydration-hydrogenation cascade reactions. This picture is consistent with our results obtained from the above hydrogenation over Pd/C that produces the furan-containing polyol without ring-opening (vide supra) and the observation by Dumesic et al. that hydrogenation, but not ring-opening, of the furan ring was the primary reaction for the furan-containing compounds when subjected to HDO conditions using metal-acid bifunctional catalysts.

To generate hydrocarbon premium liquid fuels by the HDO process, we investigated HDO of DHMF under moderate conditions (250-300° C. and 3.5 MPa H$_2$ pressure) with a number of bifunctional catalyst systems. Furoin was reported to be converted to alkanes by a two-step process, with the first step being hydrogenation to make it soluble in water, followed by subsequent HDO to avoid choking problems. As DHMF is water soluble, its HDO process can be carried out directly in water without prior hydrogenation.

After initial catalyst screening, we identified three bifunctional catalyst systems that worked well for DHMF conversion to alkanes: (1) acidic solution (H$_3$PO$_4$) and Pd/C; (2) heteropoly acid (CsH$_2$PW$_{12}$O$_{40}$) supported Pt; (3) acidic solid catalyst (TaOPO$_4$) and Pt/C. In all cases, DHMF was completely converted and no or a negligible amount of alkanes below $C_{10}$ were observed. For the Pd/C+H$_3$PO$_4$ system (Table 2-2), the alkane selectivity in the organic phase was 38%, consisting of 8.6% $C_{10}$, 17.6% $C_{11}$ and 12.2% $C_{1-2}$ alkanes.

Figure 15:
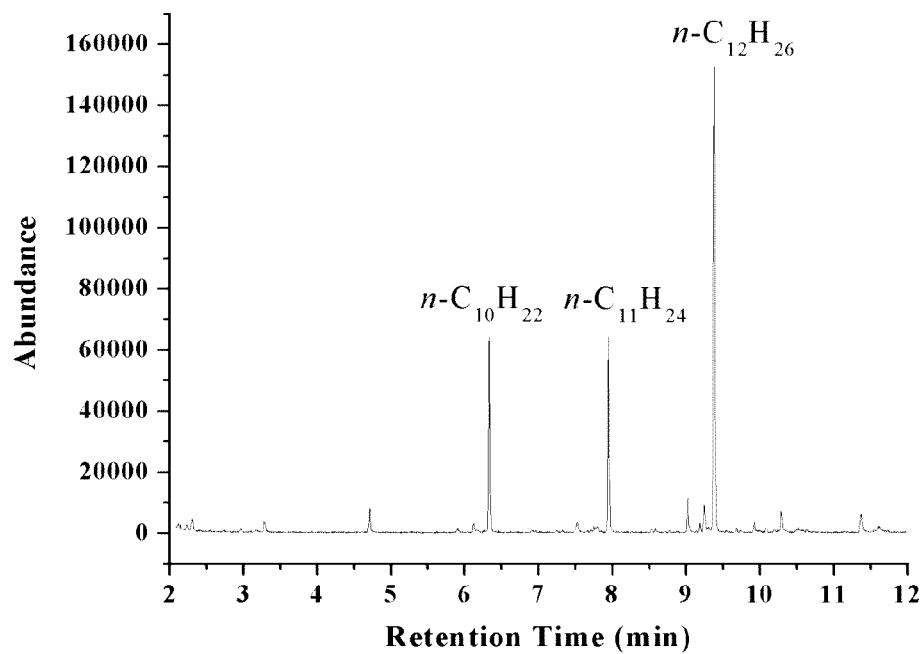
FIG. 15. GC-MS chromatogram of the organic phase products produced by HDO of DHMF catalyzed by Pt/C+ $TaOPO_4$.

TaOPO$_4$] catalyst system (Table 2-2), the highest alkane selectivity of 96% was achieved at 300° C. for 3 hours, producing 27.0% $C_{10}$ (n-decane), 22.9% $C_{11}$ (n-undecane) and 45.6% $C_{12}$ (n-dodecane), FIG. 15. It is remarkable to see the clean formation of three linear $C_{10-12}$ alkanes through this highly effective HDO process.

When compared with current methods for upgrading biomass furan compounds into biofuels, the DHMF route reported herein possesses at least the following four advantages: (1) DHMF is obtained from self-coupling of HMF, without the need for cross condensation with other petrochemicals; (2) HMF self-coupling is catalyzed by the organic NHC catalyst, which can be carried out under solvent-free conditions (neat) at 60° C. and 1 hour affording DHMF in near quantitative isolated yield; (3) owing to its solubility in water, the HDO of DHMF can be carried out directly in water, allowing for spontaneous separation of hydrocarbons from the aqueous phase; and (4) DHMF hydrodeoxygenation achieves high conversion and near quantitative selectivity towards linear $C_{10}$-$C_{12}$ alkanes with a narrow distribution of alkanes.

Accordingly, a highly effective new strategy for upgrading biomass furaldehydes to liquid fuels has been developed and has been described herein. This strategy includes the organocatalytic self-condensation (umpolung) of biomass furaldehydes into $C_{10-12}$ furoin intermediates, followed by hydrogenation, etherification or esterification into oxygenated biodiesel, or hydrodeoxygenation by metal-acid tandem catalysis into premium hydrocarbon fuels. The umpolung coupling step is carried out under solvent-free conditions, catalyzed by the organic NHC, and quantitatively selective and 100% atom-economical, all pointing to the hallmarks of an extremely green process. Liquefying the $C_{10-12}$ furoin intermediates can be readily accomplished by hydrogenation, etherification or esterification, producing oxygenated liquid biodiesel with considerably higher heating values than that of bioethanol. Most significantly, premium hydrocarbon

TABLE 2-2

Analytical results of liquid fuels in the organic phase after HDO in water.

| | Conditions | | | | | | | | Isolated liquid fuels | | |
|---|---|---|---|---|---|---|---|---|---|---|---|
| Catalysts | Temp. (° C.) | H$_2$ (psi) | Time (h) | $C_{10}$ (%) | $C_{11}$ (%) | $C_{12}$ (%) | Alkanes (%) | Oxygenated (%) | C (%) | H (%) | O (%) |
| Pd/C + H$_3$PO$_4$ | 250 | 500 | 2 | 8.6 | 17.6 | 12.2 | 38.4 | 61.6 | 75.2 | 12.6 | 12.2 |
| Pt/CsH$_2$PW$_{12}$O$_{40}$ | 250 | 500 | 2 | — | 11.3 | 40.6 | 51.9 | 48.1 | 79.4 | 13.0 | 7.6 |
| Pt/CsH$_2$PW$_{12}$O$_{40}$$^a$ | 250 | 500 | 2 | 6.1 | 15.2 | — | 24.7 | 75.3 | 77.8 | 12.6 | 9.6 |
| Pt/CsH$_2$PW$_{12}$O$_{40}$ | 300 | 500 | 2 | 4.3 | 16.8 | 18.6 | 39.7 | 60.3 | 76.2 | 12.8 | 11.0 |
| Pt/C + TaOPO$_4$ | 300 | 500 | 3 | 27.0 | 22.9 | 45.6 | 95.5 | 4.5 | 81.2 | 14.6 | 4.2 |

$^a$Biphase system with hexane/water = 50/50 mL.

Figure 14:
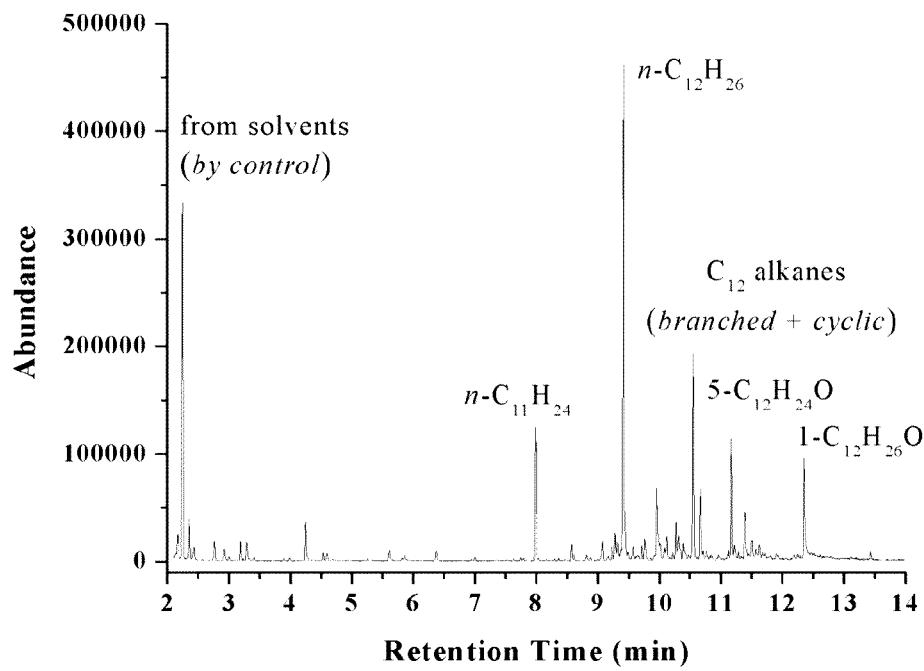
FIG. 14. GC-MS chromatogram of the organic phase products produced by HDO of DHMF catalyzed by Pt/$CsH_2PW_{12}O_{40}$.

A relatively higher alkane selectivity (52%) was obtained by Pt/CsH$_2$PW$_{12}$O$_{40}$, consisting of 11.3% $C_{11}$ and 40.6% $C_{1-2}$ alkanes (FIG. 14). We also compared the performance of two different heteropoly-acids (CsH$_2$PW$_{12}$O$_{40}$ and Cs$_{2.5}$H$_{0.5}$PW$_{12}$O$_{40}$), revealing that Pt/Cs$_{2.5}$H$_{0.5}$PW$_{12}$O$_{40}$ only converted DHMF to a trace amount of alkanes. This result shows that the stronger polyacid CsH$_2$PW$_{12}$O$_{40}$ is needed to promote the furan ring opening. Varying HDO conditions, including a biphase system of hexane/water and higher temperature at 300° C. (Table 2-2), actually lowered the alkane selectivity to 24.7% and 39.7%, respectively. The isolated liquid fuels, after the HDO process, contain noticeably higher carbon ratios (75-80%) than those by hydrogenation (60-66%). Most excitingly, utilizing the [Pt/C+ fuels can be produced through hydrodeoxygenation of the $C_{12}$ DHMF in water under moderate conditions (300° C., 3 h, 3.5 MPa H$_2$) with the bifunctional catalyst system (Pt/C+TaOPO$_4$), which yields high quality alkane fuels with 96% selectivity to linear $C_{10-12}$ alkanes, consisting of 27.0% n-decane), 22.9% n-undecane, and 45.6% n-dodecane.

Experimental Details 1,2-Di(5-hydromethyltetrahydrofuran-2-yl)ethylene glycol (DHM-THF-EG) from Hydrogenation of DHMF DHMF (0.1 g, 0.4 mmol) was dissolved in 30 mL THF and transferred to a Parr High-pressure reactor, of which loaded Pd/C (20 mol % Pd). The suspension was stirred under pressurized $H_2$ (400 Psi) and heated at 90° C. for 6 hours. The Pd/C catalyst was collected after filtration and recycled after washing with diethyl ether and dried under vacuum. The filtrate was dried overnight by high vacuum at room temperature. The obtained viscous colorless liquid was identified by $^1H$ and $^{13}C$ NMR and HRMS as DHM-THF-EG. HRMS calculated for $C_{12}H_{23}O_6$ [M+H]$^+$: 263.1495; found: 263.1489. The NMR spectra were complex due to the presence of several stereoisomers, but the absence of peaks at 5~6 ppm clearly shows that all furan ring double bonds were hydrogenated. The carbonyl double bond was also hydrogenated, indicated by $^{13}C$ NMR (no C=O signal) and HPLC-MS (no detection of carbonyl species).

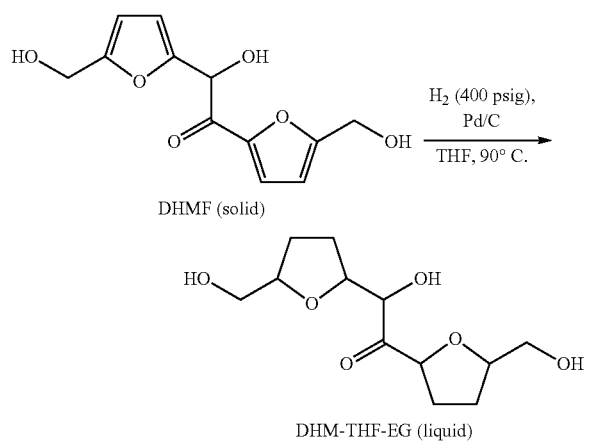

1,2-Di(5-methyl-2-furanyl)-Ethanedione (DMF-EDO) and 1,2-Di(5-methyl-furan-2-yl)ethylene glycol (DMF-EG) from Hydrogenolysis of DHMF DHMF hydrogenolysis was carried out in a benzene-water biphase system. DHMF (0.1 g, 0.4 mmol) was first dissolved in 15 mL distilled water and transferred to a Parr High-pressure reactor, of which loaded Pd/C (2 mol % Pd), HI (6 mol equiv, 57% water solution) and 20 mL benzene. The mixture was stirred under pressurized $H_2$ (400 Psi) and heated at 90° C. for 1 hour. After the reaction, the benzene phase was collected, filtered and dried by Rotovap. The resulting orange solids were identified as DMF-EDO. $^1H$ NMR in CDCl$_3$: δ 7.51 (d, $J_{H-H}$=2.7 Hz, 2H, furan ring protons), 6.23 (d, $J_{H-H}$=2.7 Hz, 2H, furan ring protons), 2.43 (s, 6H, methyl group). This compound can be further hydrogenated into liquid fuel DMF-EG using the conditions described for DHM-THF-EG.

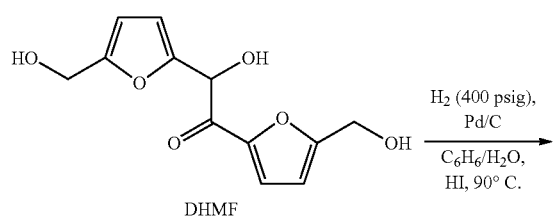

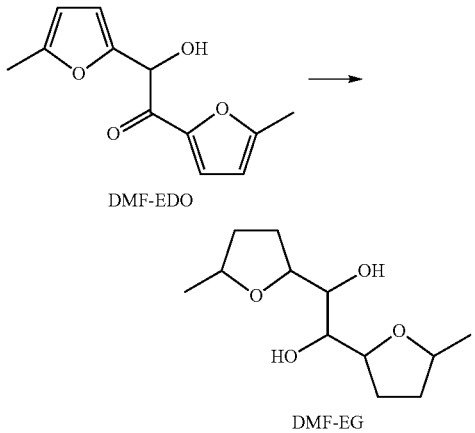

Tetrahydrofurans and methyltetrahydrofurans can be prepare by employing the corresponding substrates of Scheme 2-3 where R=H or Me. A variety of other products can be prepared by carrying out the hydrogenation reaction on other substituted furans prepare by the umpolung coupling of furaldehydes of Formula X. Additionally, DHMF can be modified prior to or after hydrogenation or hydrogenolysis to provide compounds with a variety of different substituents, as defined for substituents above. Examples include preparing various halide, amine, and amide substituted compounds, for example, as illustrated below. Substituent conversions can be carried out after hydrogenation or hydrogenolysis to provide a variety of new tetrahydrofuran compounds.

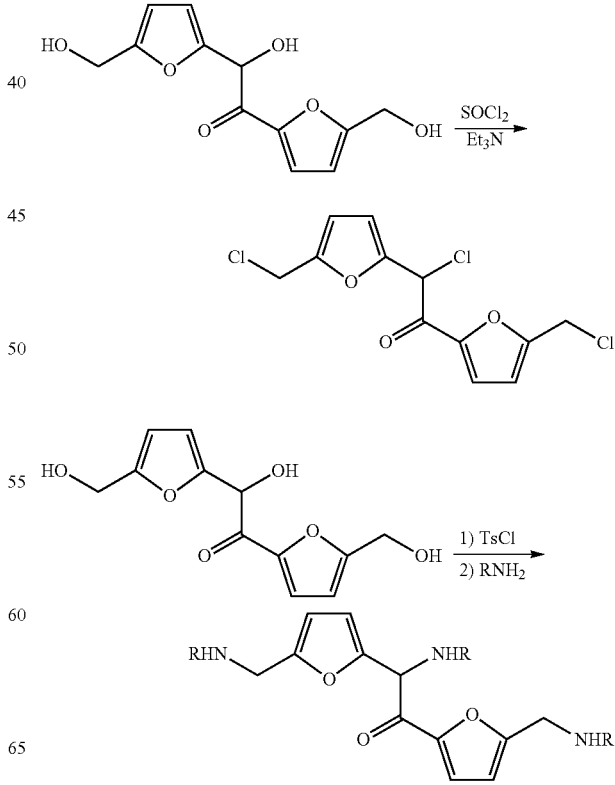

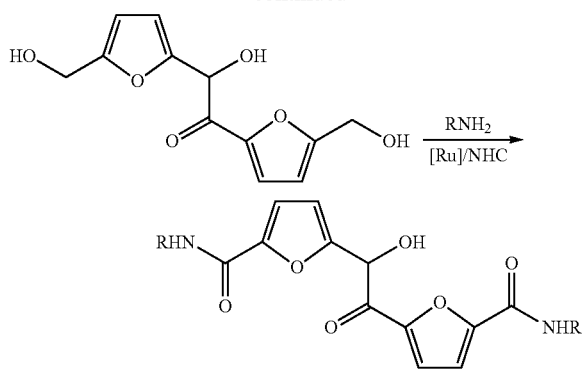

where R is substituent as defined herein, for example, alkyl, cycloalkyl, acyl, aryl (e.g., phenyl or naphthyl), benzyl, benzoyl, and the like, each optionally substituted with one or more substituents.

Etherification and Esterification of DHMF.

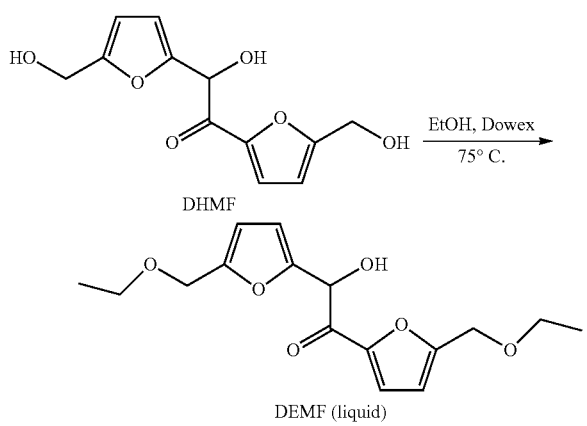

For etherification with ethanol, DHMF (0.10 g, 0.40 mmol) was dissolved in 2.0 g ethanol in a 5 mL vial. Dowex G-26 H-form resin (24 mg) was added and the vial was heated in a temperature-controlled orbit shaker (75° C., 300 rpm) for 24 hours. After the reaction, the supernatant liquid was decanted, dried by anhydrous MgSO$_4$ and removed by vacuum. 5,5'-Di(ethoxymethyl)furoin (DEMF) was obtained as viscous liquid. $^1$H NMR for DEMF (DMSO-d$_6$): δ 7.21, 6.41, 6.31, 6.26 (d, 4H, furan ring H), 5.75 (s, 1H, CHOH), 4.61 (s, 2H, CH$_2$OH), 4.38 (s, 2H, CH$_2$OH), 3.69 (q, 2H, CH$_2$CH$_3$), 3.48 (q, 2H, CH$_2$CH$_3$), 1.15-1.24 (m, 6H, CH$_2$CH$_3$). HRMS calculated for C$_{16}$H$_{21}$O$_6$ [M+H]$^+$: 309.1338; found: 309.1333. Mono-, di-, and tri-ethers of DHMF, and/or mixtures thereof, can be prepared by controlling the amount of alcohols added.

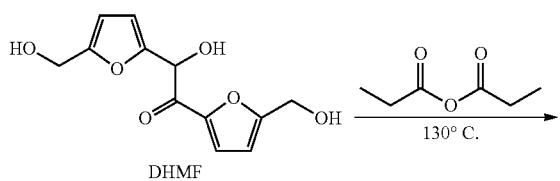

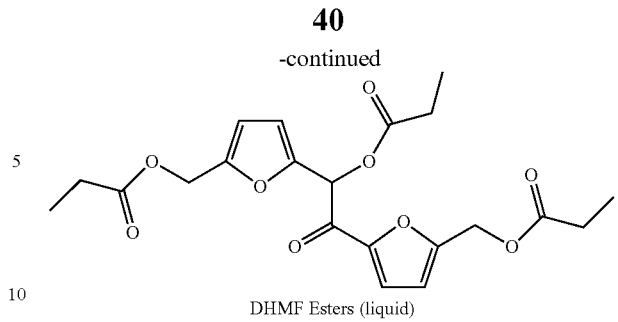

DHMF Esters (liquid)

For esterification, DHMF (0.10 g, 0.40 mmol) was mixed with propionic anhydride (0.26 g, 2.0 mmol) in a 5 mL vial and heated at 130° C. for 2 hours in a temperature-controlled orbit shaker. After the reaction, excess propanoic anhydride was removed by treatment with a saturated aqueous solution of NaHCO$_3$, and the DHMF-tripropionic ester was obtained as viscous liquid after extraction with ethyl acetate, drying with anhydrous MgSO$_4$ and further solvent removal and drying. $^1$H NMR for the DHMF-tripropionic ester (CDCl$_3$): δ 7.26, 6.54, 6.50, 6.41 (d, 4H, furan ring H), 5.19 (s, 1H, CHOH), 5.11 (s, 2H, CH$_2$OH), 5.06 (s, 2H, CH$_2$OH), 2.39 (m, 6H, CH$_2$CH$_3$), 1.14-1.25 (m, 9H, CH$_2$CH$_3$). HRMS calculated for C$_{21}$H$_{28}$NO$_9$ [M+NH$_4$]$^+$: 438.1764; found: 438.1759. Mono, di, and tri-esters of DHMF, and mixtures thereof, can be prepared by controlling the amount of propionic anhydride added.

Hydrogenation of Furoins.

Furoin (2.20 g, 11.4 mmol) was dissolved in 100 mL THF or methanol and transferred to a Parr pressure reactor, to which Pd/C (4.84 g, 10 mol % Pd to furoin) was added. The system was purged with H$_2$ for 15 minutes and heated at 90° C. for 6 hours under 400 psi H$_2$. After the reaction, Pd/C was recycled by filtration, and the filtrate was dried under vacuum. The hydrogenated furoin was obtained as liquid and subjected to elemental analysis and heating value test. 5,5'-Dimethylfuroin and DHMF were hydrogenated in a similar fashion. $^1$H NMR spectrum shows that after hydrogenation, the furan double bonds were fully hydrogenated. HRMS calculated for DHMF after hydrogenation, C$_{12}$H$_{23}$O$_6$ [M+H]$^+$: 263.1495; found: 263.1489. See Table 2-1.

Hydrodeoxygenation of DHMF.

DHMF (500 mg, 1.98 mmol) was dissolved in 50 mL distilled water and transferred to a Parr pressure reactor. To this reactor was added a catalyst, either Pd/C (0.25 g)+H$_3$PO$_4$ (0.175 mL, 0.5 wt %) or Pt/CsH$_2$PW$_{12}$O$_{40}$ (0.25 g). For the HDO by the Pt/C+TaOPO$_4$ system, the loading of DHMF, Pt/C, and TaOPO$_4$ was 0.25 g, 0.125 g, and 0.25 g, respectively. The reactor was purged with H$_2$ for 15 minutes and heated at 250° C. for 2 hours under 500 psi H$_2$ (the Pt/C+TaOPO$_4$ system was heated at 300° C. for 3 hours under 500 psi H$_2$). After the reaction, the organic phase was extracted with DCM and analyzed by GC. Alkane selectivity was reported based on the percentage of peak areas measured by GC-FID. The organic phase was further dried with anhydrous MgSO$_4$ and the solvent was removed under vacuum. The remaining oily products were subjected to elemental analysis. See Table 2-2.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An organocatalytic method comprising homocoupling 5-hydroxymethylfurfural (HMF), the method comprising contacting HMF and an ionic liquid under conditions wherein the ionic liquid forms an N-heterocyclic carbene (NHC), or by contacting HMF and a discrete NHC, to provide 5,5'-di(hydroxymethyl)furoin (DHMF), and further comprising hydrogenation, hydrogenolysis, hydrodeoxygenation, etherification, or combinations thereof, of the DHMF to provide a liquid fuel.

2. The method of claim 1 wherein the liquid fuel comprises a compound of Formula I:

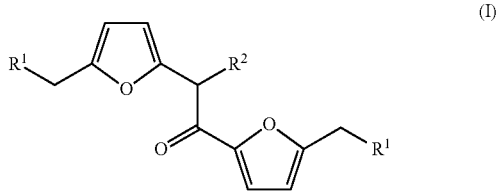

(I)

wherein each $R^1$ is independently H, OH, halo, amine, alkylamino, dialkylamino, alkoxy, or acyloxy; and $R^2$ is OH, halo, amine, alkylamino, dialkylamino, alkoxy, or acyloxy.

3. The method of claim 2 wherein the compound of Formula I is:

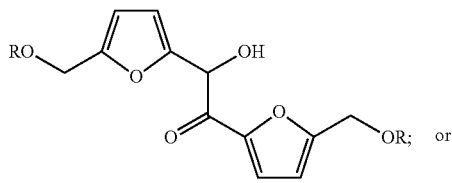

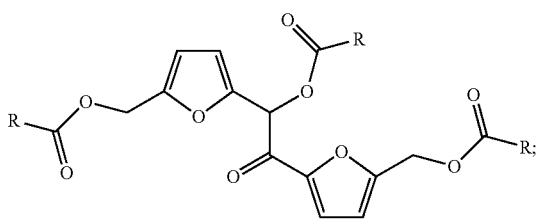

wherein each R is independently aryl or $(C_1-C_{12})$alkyl.

4. The method of claim 2 wherein the compound of Formula I is:

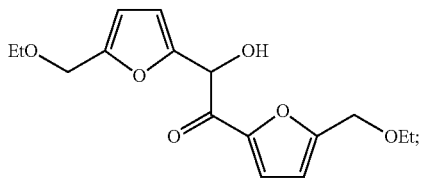

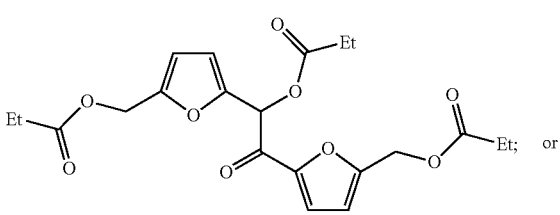

or

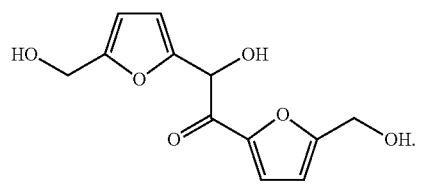

5. The method of claim 1 wherein the method comprises hydrodeoxygenation and the liquid fuel comprises decane, undecane, dodecane, or a combination thereof.

* * * * *